US007575864B2

(12) United States Patent
Bedzyk et al.

(10) Patent No.: US 7,575,864 B2
(45) Date of Patent: Aug. 18, 2009

(54) METHOD FOR THE DIRECT DETECTION OF DIAGNOSTIC RNA

(75) Inventors: Laura Bedzyk, Odessa, DE (US);
Daniel DeMarco, Wilmington, DE (US);
Richard Ebersole, Wilmington, DE (US); Raymond Jackson, Newark, DE (US); Stephen Varkey, Newark, DE (US); Rick Ye, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/135,741

(22) Filed: May 24, 2005

(65) Prior Publication Data

US 2005/0266468 A1    Dec. 1, 2005

Related U.S. Application Data

(60) Provisional application No. 60/575,003, filed on May 27, 2004.

(51) Int. Cl.
*C12Q 1/68*    (2006.01)
*C12P 19/34*    (2006.01)

(52) U.S. Cl. .......................................... 435/6; 435/91.2
(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 2002/0026046 A1* | 2/2002 | Pasloske et al. | 536/25.4 |
| 2003/0170617 A1* | 9/2003 | Pasloske | 435/5 |
| 2004/0197833 A1* | 10/2004 | Loessner | 435/7.2 |

FOREIGN PATENT DOCUMENTS

| | | |
|---|---|---|
| WO | WO 91/02817 | 3/1991 |
| WO | WO 03/008636 | 1/2003 |
| WO | WO 03/008636 A2 | 1/2003 |

OTHER PUBLICATIONS

Chiocchia et al. Highly sensitive method to detect mRNAs in individual cells by direct RT-PCR using Tth DNA polymerase. BioTechniques (1997) 22:312-318.*
Sonja Selenska -Pobell, Detection of mRNA and rNA Via Reverse Transcription and PCR in Soil. Molecular Microbial Ecology Manual 2.7.5, 1995, pp. 1-14.
Sanjay Tyagi et. al., Molecular Beacons: Probes That Fluoresce Upon Hybridization. Nature Biotechnology, 1996, pp. 303-308, vol. 14.
Carola Burtscher et. al., Evaluation of the Use of PCR and Reverse Transcriptase PCR for Detection of Pathogenic Bacteria in Biosolids From Anaerobic Digestors and Aerobic Composters, Applied and Environmental Microbiology, 2003, pp. 4618-4627, vol. 69.

Wilson, Development of Sensitive, High-Throughput One-Tube RT-PCR-Enzyme Hybridisation Assay to Detect Selected Bacterial Fish Pathogens, Diseases of Aquatic Organisms, 2003, pp. 127-134, vol. 54.
M.J. Loessner et. al., A New Procedure for Efficient Recovery of DNA, RNA, and Proteins From Listeria Cells by Rapid Lysis With a Recombinant Bacteriophage Endolysin, Applied Environmental Microbiology, 1995, pp. 1150-1152, vol. 61.
Ririe et. al., Product Differentiation by Analysis of DNA Melting Curves During the Polymerase Chain Reaction, Anal. Biochem., 1997, pp. 154-160, vol. 245.
J. Sambrook et. al., Molecular Cloning, 1989, A Laboratory Manual, Cold Spring Harbor Laboratory Press, Cold Spring Harbor, NY (Book Not Included).
T.J. Silhavy et. al., Experiments With Gene Fusions, 1984, Cold Spring Laboratory, Cold Springs, NY (Book Not Included).
F.M. Ausubel et. al., Current Protocols in Molecular Biology, 1987, Greene Publishing Assoc. and Wiley-Interscience, NY. (Book Not Included).
P. Gerhardt et. al., Manual of Methods for General Bacteriology, American Society for Microbiology, Washington, DC., 1994 (Book Not Included).
T.D. Brock, Biotechnology: A Textbook of Industrial Microbiology, 2nd Edition, Sinauer Associates, Inc, Sunderland, MA, 1989 (Book Not Included).
Collins, M. D., U. Rodrigues, et al. (1991). "Phylogenetic analysis of the genus *Lactobacillus* and related lactic acid bacteria as determined by reverse transcriptase sequencing of 16S rRNA." FEMS Microbiology Letters 77(1):5-12.
de Chateau, M. and L. Bjorck (1996). "Identification of interdomain sequences promoting the Intronless evolution of a bacterial protein family." Proc Natl Acad Sci U S A 93(16):8490-5.
Valtilingom, M., F. Gendre, et al. (1998). "Direct detection of viable bacteria, molds, and yeasts by reverse transcriptase PCR in contaminated milk samples after heat treatment." Appl Environ Microbiol 64(3): 1157-60.
el, Y., J. M. Lee, et al. (2001). "High-density microarray-mediated gene expression profiling of *Escherichla coli*." J Bacteriol 183(2): 545-56.
Vaitilingom M et al: "Direct Detection of Viable Bacteria, Molds, and Yeast by Reverse Transcriptase PCR in Contaminated Milk Samples After Heat Treatment" Applied and Environmental Microbiology, Washington, D.C., US, vol. 64, No. 3, Mar. 1998, pp. 1157-1160.
Wei Yan et al: "High-Density MMicroarray-Mediated Gene Expression Profiling of *Escherichia coli*" Journal of Bacteriology, Washington, D.C., vol. 183, No. 2, Jan. 2001, pp. 545-556.
Loessner MJ et al: "A New Procedure for Efficient Reovery of DNA, RNA, and Proteins From Listeria Cell by Rapid Lysis With a Recombinant Bacteriophage Endolysin" Applied and Environmental Microbiology, Washington, D.C., vol. 61, No. 3, Mar. 1995, pp. 1150-1152.
Chateau De M et al: "Identification of Interdomain Sequences Promoting the Intronless Evolution of a Bacterial Protein Family" Proceedings of the National Academy of Sciences of USA, National Academy of Science, Washington, D.C., vol. 93, Aug. 1996, pp. 8490-8495.

(Continued)

*Primary Examiner*—Kenneth R. Horlick
*Assistant Examiner*—David C Thomas

(57) ABSTRACT

Methods for the direct detection of diagnostic target RNA have been developed, which obviate the need for time consuming RNA purification and isolation procedures.

18 Claims, 5 Drawing Sheets

OTHER PUBLICATIONS

Collins M D et a,;: "Phylogenetic Analysis of the Genus *Lactobacillus* and Related Lactic Acid Bacteria as Determined by Reverse Transcriptase Sequencing of 16S RRNA" FEMS Microbiology Letters, Amsterdam, NL., vol. 77, No. 1, 1991, pp. 5-12.

Collins, M. D., U. Rodrigues, et al. (1991). "Phylogenetic analysis of the genus *Lactobacillus* and related lactic acid bacteria as determined by reverse transcriptase sequencing of 16S rRNA." FEMS Microbiology Letters 77(1): 5-12.

de Chateau, M. and L. Bjorck (1996). "Identification of interdomain sequences promoting the intronless evolution of a bacterial protein family." Proc Natl Acad Sci U S A 93(16): 8490-5.

Loessner, M. J., A. Schneider, et al. (1995). "A new procedure for efficient recovery of DNA, RNA, and proteins from Listeria cells by rapid lysis with a recombinant bacteriophage endolysin." Appl Environ Microbiol 61(3): 1150-2.

Vaitilingom, M., F. Gendre, et al. (1998). "Direct detection of viable bacteria, molds, and yeasts by reverse transcriptase PCR in contaminated milk samples after heat treatment." Appl Environ Microbiol 64(3): 1157-60.

Wei, Y., J. M. Lee, et al. (2001). "High-density microarray-mediated gene expression profiling of *Escherichia coli*." J Bacteriol 183(2): 545-56.

International Search Report and Written Opnion of the International Searching Authority PCT/US2005/018838, Mailed Dec. 1, 2006.

Walz G, Zanker B, (1989) Sequential Effects of interleukin 2 -diptheria toxin fusion protein on T cell Activation, Proc. Natl. Acad. Sci. USA 86(23):9485-88.

QuantumRNA beta Actin Internal Standards Kit (Cat. #1720), Instruction Manual Version 0607, (2006) Ambion/Applied Biosystems, Austin, TX USA.

Linear Acyrlamide Cat # AM9520, Product Insert (2006) Ambion/Applied Biosystems, Austin, TX USA.

Application Note, MELT Total Nucleic Acid Isolation System: a new technology for hands free tissue disruption, RNA preservation and total nucleic acid purification, Nature Methods 2: 2005.

Weigers U., and Hilz H., (1971) A new method of using "Proteinase K" to prevent mRNA degradation during isolation from HeLa Cells, Biochem. Biophys. Res. Com 44(2):513-519.

* cited by examiner

SEQUENCE LISTING

<160> NUMBER OF SEQ ID NOS: 11

<210> SEQ ID NO 1
<211> LENGTH: 18
<212> TYPE: DNA
<213> ORGANISM: artificial
<220> FEATURE:
<223> OTHER INFORMATION: synthetic

<400> SEQUENCE: 1
agcttgctct tccaaagt                                                 18

<210> SEQ ID NO 2
<211> LENGTH: 19
<212> TYPE: DNA
<213> ORGANISM: artificial
<220> FEATURE:
<223> OTHER INFORMATION: synthetic

<400> SEQUENCE: 2
aagcagttac tcttatcct                                           19

<210> SEQ ID NO 3
<211> LENGTH: 20
<212> TYPE: DNA
<213> ORGANISM: artificial
<220> FEATURE:
<223> OTHER INFORMATION: synthetic

<400> SEQUENCE: 3
tccgcaatgg acgaaagtct                                          20

<210> SEQ ID NO 4
<211> LENGTH: 23
<212> TYPE: DNA
<213> ORGANISM: artificial
<220> FEATURE:
<223> OTHER INFORMATION: synthetic

<400> SEQUENCE: 4
ttacgatccg aaaaccttct tca                                      23

<210> SEQ ID NO 5
<211> LENGTH: 18
<212> TYPE: DNA
<213> ORGANISM: artificial
<220> FEATURE:
<223> OTHER INFORMATION: synthetic

<400> SEQUENCE: 5
acggagcaac gccgcgtg                                            18

<210> SEQ ID NO 6
<211> LENGTH: 21
<212> TYPE: DNA
<213> ORGANISM: artificial
<220> FEATURE:
<223> OTHER INFORMATION: synthetic

<400> SEQUENCE: 6
gctgataccg cccaagagtt c                                        21

<210> SEQ ID NO 7
<211> LENGTH: 21
<212> TYPE: DNA
<213> ORGANISM: artificial
<220> FEATURE:
<223> OTHER INFORMATION: synthetic

<400> SEQUENCE: 7
caggatgtga tgagccgaca t                                        21

<210> SEQ ID NO 8
<211> LENGTH: 20
<212> TYPE: DNA
<213> ORGANISM: artificial
<220> FEATURE:
<223> OTHER INFORMATION: synthetic

<400> SEQUENCE: 8
tcgacggcgg tgtttggcac                                          20

<210> SEQ ID NO 9
<211> LENGTH: 16
<212> TYPE: DNA

```
<213> ORGANISM: artificial
<220> FEATURE:
<223> OTHER INFORMATION: synthetic

<400> SEQUENCE: 9
ttgccagcgc gtcatg                                                        16

<210> SEQ ID NO 10
<211> LENGTH: 21
<212> TYPE: DNA
<213> ORGANISM: artificial
<220> FEATURE:
<223> OTHER INFORMATION: synthetic

<400> SEQUENCE: 10
ccaccttcct ccggtttatc a                                                  21

<210> SEQ ID NO 11
<211> LENGTH: 23
<212> TYPE: DNA
<213> ORGANISM: artificial
<220> FEATURE:
<223> OTHER INFORMATION: synthetic

<400> SEQUENCE: 11
cgggaactct agggagactg ccg                                                23
```

METHOD FOR THE DIRECT DETECTION OF DIAGNOSTIC RNA

FIELD OF THE INVENTION

The invention relates to the field of diagnostic microbiology. More specifically, methods are provided that allow for the rapid and sensitive detection of diagnostic target RNA from samples without the need for RNA purification or isolation.

BACKGROUND OF THE INVENTION

It is often desirable to assay for the presence of bacteria in various clinical, food, environmental, or other experimental samples to identify contaminants or pathogens. Bacterial RNA, typically ribosomal RNA (rRNA) or in some cases, messenger RNA (mRNA) may be assayed to assess the presence or absence of a bacterial species. For some important bacterial species, specific probes have been developed, which are capable of detecting a particular RNA molecule belonging to that bacterial species, thereby allowing its detection even when in the presence of other bacterial species. Probes may be used as primers in the RT-PCR assay method to detect a specific RNA molecule through its reverse transcription into DNA, followed by amplification of its copy DNA using the polymerase chain reaction. The entire bacterial detection process generally involves the growth of bacteria and extraction of bacterial RNA, followed by the RT-PCR reaction and product detection. The bacterial growth and RNA preparation steps are time consuming. Attempts have been made to shorten and simplify the overall bacterial detection process.

The bacterial detection process was improved through the use of highly specific probes that allow detection of a target bacterial strain in the presence of large numbers of non-target bacteria by Burtscher and Wuertz (Applied and Environmental Microbiology 2003, 69:4618-4627). *Salmonella* spp., *Listeria monocytogenes*, and *Staphylococcus aureus* were detected in organic waste samples using probes specific for a different mRNA from each species in RT-PCR assays. Detection was described as being highly sensitive and reliable for the presence of extracted RNA species. In this report, the improvement to bacterial detection was that cell plating and further differentiation of isolated colonies were not necessary due to the high sensitivity and specificity of the RT-PCR assay. However, no simplification of the RNA preparation process was made; the bacterial RNA was extracted using the RNeasy-Mini kit (Qiagen) that involves multiple steps including lysozyme treatment, vortexing in a kit supplied buffer, centrifugation, application of the supernatant to a column, and elution.

Highly sensitive RT-PCR assays were also used in Wilson and Carson (Diseases of Aquatic Organisms 2003, 54:127-134) to detect bacterial fish pathogens. The improvement made to bacterial detection in this report was the development of a high through-put system involving a single tube RT-PCR-enzyme hybridization assay. No simplification was made to the RNA preparation process. The bacterial RNA assayed in this report was extracted and purified using an RNAqueouS™-PCR (Ambion) extraction kit or another procedure also involving binding to glass fiber filters.

A method of using RT-PCR to amplify rRNA and mRNA recovered by direct lysis from environmental samples was used in S. Selenska-Pobell (Molecular Microbial Ecology Manual (1995), 2.7.5/1-2.7.5/14. Editors: Akkermans, Antoon D. L.; Van Elsas, Jan Dirk; De Bruijn, Frans J. Publisher: Kluwer, Dordrecht, Neth.) In this report, "direct lysis" refers to the purification of RNA directly from an environmental sample as opposed to isolating and growing bacteria from the environmental sample prior to RNA purification. Again, no simplification was made to the method of RNA preparation, which included steps of lysing, phenol/chloroform-isoamyl alcohol extraction, centrifugation, chloroform extraction, precipitation, drying and resuspension.

Although the methods described above are useful for the detection of RNA species, they still suffer from the need for a multistep process to purify and isolate the RNA species prior to analysis. Such processes add cost and time to the analysis. A need still remains for a process for the rapid identification of bacteria based on diagnostic RNA species, without the additional steps of RNA isolation or purification. Applicants have solved the stated problem by providing a method for RNA detection which requires no RNA isolation or purification of the sample.

SUMMARY OF THE INVENTION

The present invention provides a method for directly detecting diagnostic target RNA from a bacterial cell sample. The bacterial cell sample is directly contacted with the RT-PCR reaction composition which is then subjected to thermocycling for production and detection of an amplified diagnostic target DNA product. In another aspect, the bacterial cell sample is directly contacted with an RT reaction composition and incubated to produce a cDNA product, followed by contact with a PCR composition which is then subjected to thermocycling for production and detection of an amplified diagnostic target DNA product. In a different aspect, the bacterial cell sample is treated with a lysing agent prior to contact with the RT-PCR, or RT compositions. In yet a different aspect, the product of RT reaction itself is detected without coupling to PCR amplification. In another aspect, at least one RNase inhibitor is added to the bacterial cell sample prior to contact with the RT-PCR, or RT compositions. In all aspects, the invention is carried out without any RNA purification step.

Optionally, the sample containing the bacterial cell is pretreated with an agent such as heat, enzyme, lysis buffer and/or physical shearing to enhance the availability of RNA. In a further aspect, the agent may be a viral endolysin. The present method may be used in a food processing context to detect bacteria on surfaces used in the processing of food processing or with which food comes in contact.

Also provided is a kit for the direct detection of a diagnostic target RNA from a bacteria which includes instructions that describe the present method and either an RT or RT-PCR composition, depending on whether a cDNA product from the diagnostic target RNA is directly detected, or is amplified. The RT-PCR or RT compositions may include any of the following elements: at least one primer complementary to the diagnostic target RNA; a heat activated thermostable polymerase; a reverse transcriptase enzyme; dNTPs; appropriate buffers; Rnase inhibitor.

BRIEF DESCRIPTION OF THE FIGURES AND SEQUENCE DESCRIPTIONS

The invention can be more fully understood from the following detailed description and the accompanying sequence descriptions, which form a part of this application.

FIG. 1 shows gel electrophoresis analysis of RT-PCR and PCR products from bacterial cell samples.

a. FIG. 2 shows a comparison of CT values for three different RT-PCR reaction sets using bacterial cell samples.

Figure 1A:
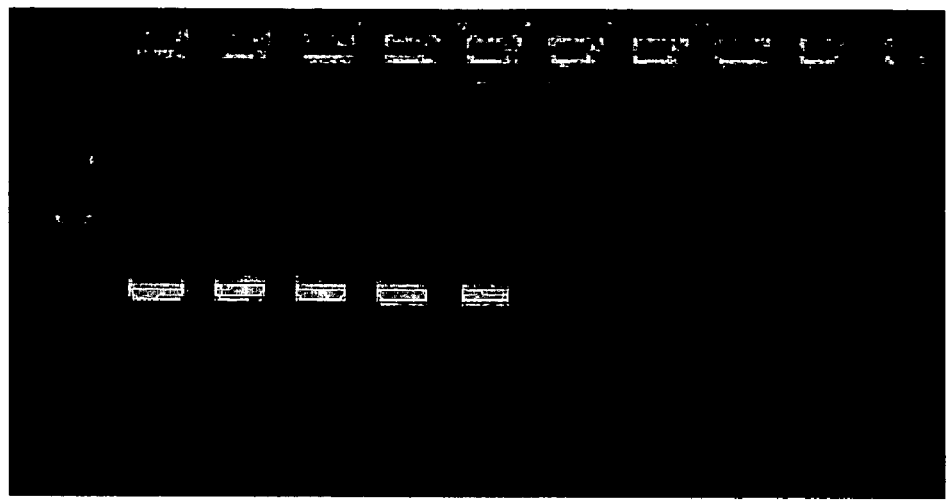

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the sequence of the Lis-F primer.
SEQ ID NO:2 is the sequence of the Lis-R primer.
SEQ ID NO:3 is the sequence of the 16S-373F primer.
SEQ ID NO:4 is the sequence of the 16S-436-R primer.
SEQ ID NO:5 is the sequence of the 16S-394T tag.
SEQ ID NO:6 is the sequence of the 16S-2455F primer.
SEQ ID NO:7 is the sequence of the 16S-2523R primer.
SEQ ID NO:8 is the sequence of the 16S-2479T primer.
SEQ ID NO:9 is the sequence of the 16S-1108F primer.
SEQ ID NO:10 is the sequence of the 16S-1169R primer.
SEQ ID NO:11 is the sequence of the 16S-1125T primer.

DETAILED DESCRIPTION OF THE INVENTION

The present invention describes a method of directly detecting diagnostic target RNA in a bacterial sample with the omission of an RNA purification process, whereby the type(s) of bacteria present in the sample may be identified. The method is useful in a variety of applications in which rapid detection of a diagnostic RNA species is needed from samples containing mixed populations of cells. Specific commercial applications for such technology include the medical and veterinary diagnostic fields as well as the field of detection of food borne bacterial pathogens.

The following abbreviations and definitions are to be used for the interpretation of the claims and the specification.

| Abbreviations | |
|---|---|
| BHI | Brain Heart Infusion Culture Media |
| BSA | Bovine Serum Albumin |
| CT | Cycle Threshold |
| Der | Derivative |
| DEPC | Diethyl pyrocarbonate |
| DMSO | Dimethyl Sulfoxide |
| dNTP | Nucleotides |
| DNA | Deoxyribonucleic acid |
| FB | Fraser Broth |
| PBS | phosphate buffered saline |
| PCR | polymerase chain reaction |
| RNA | Ribonucleic acid |
| mRNA/DNA | messenger RNA/DNA |
| rRNA/rDNA | ribosomal RNA/DNA |
| RT | Reverse transcription |
| Rt | Reverse transcriptase |
| RT-PCR | Reverse transcription polymerase chain reaction |
| TSA | Trypticase soy agar |
| TSB | Trypticase soy broth |

Definitions

As used herein, the term "bacterial cell" means any prokaryotic cell having RNA suitable for analysis or detection. As used herein, the term "bacterial cell" means any prokaryotic cell having RNA suitable for analysis or detection. Bacterial cells of the invention may be living, dead, or damaged, that is, having disruptions in the cell wall or cell membrane. The bacterium can be in any of its life cycle forms, for example, vegetative, stationary, or spore.

As used herein, the term "Colony Forming Units" or "cfu" refers to the number of cells in a sample that produce a colony on an agar plate. Cfu may also refer to the number of cells producing colonies that are expected to be in a sample by comparison to a similar assayed sample. This is an equivalent number of cfu, which is referred to as simply cfu or cells. Likewise, cells or cfu may also refer to the equivalent number of cfus present in a sample prior to treatment or lysis.

As used herein, the term "RNA" refers to a nucleic acid molecule comprising a ribose sugar as opposed to a deoxyribose sugar as found in DNA. As used herein, RNA refers to all species of RNA including messenger RNA (mRNA), ribosomal RNA (rRNA), transfer RNA (tRNA) as well as small RNA species that have regulatory function. "Small RNA species" have a specific meaning and refer to untranslated RNAs with housekeeping or regulatory roles in bacteria. "Small RNA species" are not rRNA or tRNA.

As used herein, the term "RNase inhibitor" refers to a chemical or other agent having the ability to interfere with the action of RNase enzymes, such as the endogenous RNases produced by most bacterial cells. An Rnase is a ribonuclease, an enzyme that catalyzes the cleavage of nucleotides in RNA.

As used herein, the term "diagnostic target RNA" refers to an RNA molecule or fragment that is diagnostic of a particular bacteria.

As used herein, the term "diagnostic target DNA product" refers to a DNA molecule or fragment that is transcribed from a diagnostic target RNA or is synthesized using transcribed DNA copies of the diagnostic target RNA as template.

As used herein, the term "reverse transcription followed by polymerase chain reaction", or "RT-PCR", refers to a technique for synthesizing and amplifying a DNA molecule with a sequence that is a copy of an RNA sequence. RT-PCR is useful for detecting RNA species such as in quantitative analysis of gene expression, as well as for producing DNA copies of RNA for use in cloning, cDNA library construction, probe synthesis, and signal amplification in in situ hybridizations. The technique consists of two parts: synthesis of cDNA from RNA by reverse transcription (RT), and amplification of a specific cDNA by polymerase chain reaction (PCR). Reverse transcriptase is an RNA dependent DNA polymerase that catalyses the polymerization of nucleotides using template RNA or the RNA molecule in an RNA:DNA hybrid.

As used herein, the term "primer" refers to an oligonucleotide, synthetic or naturally occurring, which is capable of acting as a point of initiation of nucleic acid synthesis or replication along a template strand when placed under conditions in which the synthesis of a complementary strand is catalyzed by a polymerase. Within the context of reverse transcription, primers are composed of nucleic acids and prime on RNA templates. Within the context of PCR, primers are composed of nucleic acids and prime on DNA templates.

As used herein, the term "RT-PCR reaction composition" means a composition having all the elements required to perform reverse transcription—polymerase chain reaction including but not limited to: primers having specificity for the sequence of the diagnostic target RNA; a heat activated thermostable polymerase; a reverse transcriptase; dNTPs and appropriate buffers. Optionally these compositions may include an RNase inhibitor as defined herein.

As used herein, the term "an RT reaction composition" means a composition having all the elements required to synthesize a DNA product from an RNA template, including but not limited to a reverse transcriptase enzyme, nucleic acid primer(s) complementary to the target RNA, dNTPs and the appropriate buffers and may contain detection dyes or probes. Optionally these compositions may include an RNase inhibitor as defined herein.

As used herein, the term "PCR reaction composition" means a composition having all the elements required to amplify a DNA template, including but not limited to nucleic acid primers, thermostable polymerases, dNTPs and appropriate buffers and may contain detection dyes or probes. Optionally these compositions may include an RNase inhibitor as defined herein.

As used herein, the term "amplification product" refers to nucleic acid fragments that are produced during a primer directed amplification reaction. Typical methods of primer directed amplification include polymerase chain reaction (PCR), RT-PCR, ligase chain reaction (LCR) or strand displacement amplification (SDA).

As used herein, the term "RNA purification" refers to a process designed to isolate RNA from all other cellular components; this may also be termed RNA extraction. There are a number of different RNA purification processes that may include steps such as phenol-chloroform extraction, binding to a column or filter, and precipitation.

As used herein, the term "lysis" means perturbation or alteration to a cell wall facilitating access to or release of the cellular RNA or DNA. Neither complete disruption nor breakage of the cell wall is an essential requirement to the concept of lysis.

As used herein, the term "lysing agent" means any agent or condition, or combination of agents or conditions, suitable for the lysing of bacterial cells. Lysing agents may comprise enzymes (such as lysozyme, or a bacteriophage lytic enzyme) or chemicals (such as chloroform), mild detergents, lysing buffers, heat or may involve physical shearing means such as the use of sonication, bead mills, French presses and the like. Lysing agents are well known in the art.

As used herein, the term "thermocycling" refers to the entire pattern of changing temperature used during an RT-PCR or PCR assay. This process is common and well known in the art. See, for example, Sambrook supra; and U.S. Pat. No. 4,683,202 to Mullis et al. and U.S. Pat. No. 4,683,195 to Mullis et al. In general, PCR thermocycling includes an initial denaturing step at high temperature, followed by a repetitive series of temperature cycles designed to allow template denaturation, primer annealing, and extension of the annealed primers by the polymerase. Generally, the samples are heated initially for 2-5 minutes to denature the double stranded DNA. Then, in the beginning of each cycle, the samples are denatured for 20 to 60 seconds, depending on the samples and the type of instrument used. After denaturing, the primers are allowed to anneal to the target DNA at a lower temperature, from about 40° C. to about 2° C. for about 20 to 60 sec. Extension of the primer(s) by the polymerase is often carried out at a temperature ranging from about 65° C. to about 72° C. The amount of time used for extension will depend on the size of the amplicon and the type of enzymes used for amplification. The current rule of thumb is 1 min for 1 kb of DNA to be amplified. In addition, the annealing can be combined with the extension step, resulting in a two step cycling. The RT-PCR thermocycling reaction includes an initial incubation in the range of about 30° C. to 70° C. for about 10 to 15 min for the reverse transcription reaction. Thermocycling may include additional temperature shifts used in RT-PCR and PCR assays.

As used herein, the term "CT", "Cycle Threshold", "Ct", or "Threshold cycle" refers to the cycle during thermocycling in which the increase in fluorescence due to product formation reaches a significant level above background signal.

As used herein, the term "Der" or "Derivative" refers to the derivative of the rate of change in fluorescence with respect to temperature during the dissociation of the RT-PCR or PCR products, which is also referred to as derivative peak value.

As used herein, the term "direct detection" refers to the assay for the presence of a diagnostic target RNA without prior purification of RNA from the target bacteria.

As used herein, the term "food processing context" refers to any surface within, in, on or by a site, as well as the site itself, where foodstuff alone or combination with other matter is manipulated into a form that results in either an ingestible product or byproduct. Such contexts include, but are not limited to, industrial and institutional food processing plants. Ingestible means able to be taken into the body and is not limited to the process of eating.

As used herein, the term "medical context" refers to any surface within, in, on or by a site, as well as the site itself, where health professionals practice, including, but not limited to, hospitals, convalescent centers, diagnostic laboratories, imaging centers, and patient residences.

As used herein, samples taken from a food processing context and samples taken from a medical context refer to any portion of bacterial content obtained by any method for sampling, random or nonrandom, using by any method for acquiring bacteria from those contexts as described above.

Source of Bacterial Cells

The present invention provides an improved method and a kit for the detection of bacterial cells that may be applied to a variety of samples. Bacterial cells may be detected in the following types of samples: biological, experimental, medical, agricultural, industrial, environmental, food, or food precursor origin. This list is exemplary not exhaustive. In particular, the invention may be applied to detection of contaminants or pathogens that are, or may be, causative agents of disease. Food processing, handling and preparation area samples are preferred as these are of particular concern for the spread and contamination of bacterial pathogens in the food supply.

Obtaining bacterial cells for a detection assay from a sample may be by way of collecting a liquid sample, extracting a solid or semi-solid sample, swabbing a surface, or additional technique. Bacterial cells may be assayed directly if the existing concentration adequately provides target RNA for an RT-PCR reaction. Alternatively, bacterial cells may be concentrated by methods such as centrifugation, binding to a surface through immunoadsorption or other interaction, or filtration. In addition, the bacterial cell number may be increased by growing the cells on culture plates or in liquid medium prior to concentration or direct assay.

Typical bacteria suitable within the context of the invention are gram-negative and gram-positive bacteria including, but not limited to, *Listeria, Escherichia, Salmonella, Campylobacter, Clostridium, Helicobacter, Mycobacterium, Staphylococcus, Camplobacter, Enterococcus, Bacillus, Neisseria, Shigella, Streptococcus, Vibrio, Yersinia, Bordetella, Borrelia,* and *Pseudomonas*.

The present method and present kit are particularly useful for detecting bacteria in a food source, food processing context or environmental or medical context. The food sources of greatest interest for the practice of the present method include flesh foods—meat, fish, poultry—dairy products, fruits and mixtures of these, whether cooked or not. In addition, the present method is useful in detecting bacteria on surfaces where food is, has or will be prepared. Further, the present method is useful in hospitals, medical centers, convalescing and nursing institutions and the like for the detection of bacteria on various surfaces, especially to identify and minimize sources of disease within the medical institution. Thus, sample sources for detecting bacteria via the present method may include but are not limited to materials that have come into contact with surfaces where food is, has or will be prepared and materials having contacted surfaces in medical contexts, such as by swabbing or by other methods for obtaining sources listed above.

Target RNA

RNA types that may be assayed as diagnostic target RNA include rRNA, mRNA, transfer-RNA (tRNA), or other RNA polynucleotides of a bacterial cell. Species of rRNA include 5S, 16S, and 23S polynucleotides, which may contain one or more sub-sequences characteristic of a group of related bacteria. The presence of the characteristic sub-sequence identifies, i.e. detects, the bacterial type of interest in the sample. The detection capacity of the characteristic sequence is variable and depends on the level of relatedness of the bacteria to be detected by the assay. For example, the detection of any Listeria species in a sample may rely on a characteristic sub-sequence that does not have as fine a detection capacity as that sub-sequence needed to detect only Listeria monocytogenes. Thus, a characteristic sub-sequence may have an identifying capacity that varies depending on which bacteria is to be detected relative to the total content of bacteria in the sample. For this reason, the instant method has broad applicability and is not limited to a specific identifying capacity for a diagnostic target RNA, or to any type of RNA used as the target.

Other RNA polynucleotides may be used as diagnostic target RNA so long as they contain unique sub-sequences that adequately distinguish among bacteria at the desired relatedness level. Examples can be identified from tRNA and mRNA species, as well as from any RNA produced in a bacterial cell that includes one or more characteristic sub-sequence.

Primers may be designed by one skilled in the art to prime the synthesis of a copy DNA using the target RNA as template in a reverse transcription reaction. One skilled in the art will also know how to design pairs of primers for the amplification of the unique sub-sequences of the target RNA using the copy DNA as template in PCR. It is well known in the art that primers used synchronously in PCR should have similar hybridization melting temperatures.

The diagnostic target RNA within the bacterial cell must be made accessible to the RT or RT-PCR reaction composition. In one aspect of the instant invention, the target RNA becomes accessible through the conditions of the RT or RT-PCR reaction itself. After being collected, the bacterial cell sample may be directly added to the reaction composition, which then undergoes thermocycling.

Alternatively, the cells may be pretreated with a variety of agents or means that modify them without purification of RNA. For example, cells may be pre-treated by exposure to heat, various chemicals, enzymes, mild detergents and mild physical shearing. This pre-treatment can result in cell lysis.

In one aspect, a lysing agent may be added to the bacterial cell(s) prior to contact with the RT or RT-PCR reaction composition. The use of lysing agents for bacterial cells is well known to those of skill in the art. Lysing agents include but are not limited to chemicals, enzymes, physical shearing, osmotic agents and high temperature. By the term "lysis buffer" is meant a buffer that contains at least one lysing agent.

Typical enzymatic lysing agents include, but are not limited to, lysozyme, glucolase, zymolose, lyticase, proteinase K, proteinase E and viral endolysins and exolysins. The viral endolysins and exolysins are from bacteriophages or prophage bacteria and combinations of these.

Typical viral endolysins include but are not limited to endolysins from Listeria bacteriophages (A118 and PLY118), endolysins from bacteriophage PM2, endolysins from the B. subtilis bacteriophage PBSX, endolysins from Lactobacillus prophages Lj928, Lj965 and bacteriophage Phiadh, endolysin (Cpl-1) from the Streptococcus pneumoniae bacteriophage Cp-1 and the bifunctional peptidoglycan lysin of Streptococcus agalactiae bacteriophage B30. These last two have different bacterial strain specificity. Also contemplated are two-component, that is, holin-endolysin, cell lysis genes, holWMY and lysWMY of the Staphylococcus wameri M phage varphiWMY Endolysin combinations of these are also contemplated. For a discussion of viral lysis, see especially, Loessner, M J et al. (1995) Applied Environmental Microbiology I 61:1150-1152, which is incorporated herein by reference.

Typical lysing agents that achieve physical shearing include zirconia-silica beads, sonication or a French press. A combination of physical shearing such as vortexing in the presence of a chemical agent, such as chloroform, is a further means of lysing bacterial cells. Additionally, high temperatures are also effective in lysing cells as described above. Lysis buffers together with a heat treatment may improve lysis.

Many of the above agents tend to be non-selective as to which cells in a sample are lysed. As a consequence, contaminating organisms and natural flora contained in test samples, as well as the cells targeted for detection, may be lysed during treatment. This non-specificity increases the quantity of cellular RNAase released into the media and can greatly diminish the stability and quality of the target RNA for detection.

In contrast, viral lysing agents and engineered materials providing viral lysing activity specifically lyse only target cells, that is perform specific lysis. This means that using these lysing agents minimize RNase activity in the sample and enhance the survival and detectability of the RNA targeted for detection. Importantly, in applications where specific lysis is desired, viral endolysins and engineered materials providing endolysin activity are particularly useful. For example, when the cells of a specific bacteria within the sample are desired to be lysed, a particular viral endolysin may be used. The use of viral endolysins for lysing specific bacteria cells is well known in the art. The use of a viral endolysin in the lysis of bacterial cells is exemplified by the XJa Autolysis™ strain of E. coli, which is readily lysed by induction of a gene expressing the lambda endolysin and which is a commercial product of Zymo Research (Orange, Calif.).

The particular cell lysing agent employed is not limited in the instant invention. When the lysing agent is used with the bacterial cell sample, the whole or a portion of that sample may be used for RT-PCR detection. A portion of the sample may include targets from less than one bacterial cell.

Besides using viral endolysins, pre-treatment with heat may also be particularly useful. Incubation of the sample in the range of temperature from about 50° C. to less than about 100° C. may improve the accessibility of bacterial RNA as a template for RT or RT-PCR. This heat pretreatment may be for a time period in the range of about 1 minute to about 60 minutes, with treatments of 1 to 20 minutes being typical, depending on the temperature of incubation. Heat treatment may include multiple incubations at different temperatures. Heat treatment may be in the presence or absence of RNase inhibitor as described below. Particularly useful treatments are at about 50° C. for about 5 to 20 min in the presence of RNase inhibitor, and at about 95° C. for about 1 to 5 minutes without RNase inhibitor or about 1 to 10 minutes with RNase inhibitor.

At least one RNase inhibitor may be added to the bacterial cell(s). Typically, inhibitors and their concentrations are chosen so as to not interfere with any of the primer directed amplification processes and components. RNase inhibitors are known to those of skill in the art and include chemicals such as guanidinium isothiocyanate and diethyl-pyrocarbonate, protein inhibitors such as SuperaseIn™ (Ambion), RNase Block (Stratagene), human placental ribonuclease inhibitor and porcine liver RNase inhibitor (Takara Mirus Bio), anti-nuclease antibodies such as Anti-Rnase (Novagen) and Ribonuclease Inhib III (PanVera), and reagents such as RNAlater™ (Ambion) and RNA protect Bacteria Reagent (Qiagen).

Assay Methods

In the present method, the presence of diagnostic target RNAs of bacterial cells is tested by reverse transcription alone or by reverse transcription and polymerase chain reaction. When used together, reverse transcription and polymerase chain reaction may be performed sequentially in two steps, or together in one step with all reaction composition reagents being added to the bacterial cell sample.

Incubation of the bacterial cell sample in the reverse transcription reaction composition allows a DNA copy from the target RNA to be synthesized. The RT composition includes a primer that hybridizes to the target RNA to prime the synthesis of the copy DNA. In addition, the RT composition includes dNTPs, $MgCl_2$, a reverse transcriptase and a reverse transcriptase buffer. More than one primer may be included if it is desired to make DNA copies from more than one target RNA. Additionally the RT composition may optionally contain an RNase inhibitor as described herein.

The product of the reverse transcription reaction may be detected directly, or a sample of this reaction may be transferred to another assay tube containing PCR composition including a pair of primers that initiate synthesis of the desired segment of DNA from the reverse transcribed template. In addition, the PCR composition contains dNTPs, a thermostable DNA polymerase such as Taq polymerase, and polymerase buffer. More than one pair of primers may be included if synthesis of multiple segments of DNA is desired. Also a single new primer may be added that will amplify a DNA segment with the original RT-PCR primer as the second primer of the pair.

Additional reverse transcriptases that may be used include, but are not limited to, HIV Reverse Transcriptase (Ambion), Transcriptor Reverse Transcriptase (Roche), Thermoscript Reverse Transcriptase (Invitrogen). Additional DNA polymerases that may be used include, but are not limited to, Pfu, Vent, and Sequitherm DNA Polymerase (EPICENTRE).

Regardless of whether the RT-PCR is carried out as two steps or one step, the RT step is run first and typically consists of a single temperature incubation at a temperature of between about 37° C. and about 70° C. Different temperatures are appropriate for different Rt enzymes and different primers, as is known to one skilled in the art. The subsequent PCR reaction typically consists of an initial incubation at about 94° C. to about 96° C. for about 6 to about 15 minutes. This step is used to denature the cDNA and also to activate heat activated Taq polymerase enzymes. This is then followed by multiple cycles of amplification of the cDNA target.

Three operations are performed during each cycle: target denaturation, primer annealing and primer extension. Target denaturation typically occurs at greater than about 90° C. Primer annealing temperature is dictated by the melting temperature of the specific primers used in the reaction and primer extension is performed at temperatures ranging from about 60° C. to about 72° C. depending on the thermostable polymerase being used. When primer annealing and extension are performed at the same temperature, this is a two temperature PCR compared with a three temperature PCR in which each of the three steps occur at a different temperature. After the amplification phase is complete, a final extension time is typically added to ensure the synthesis of all amplification products.

The instant invention also provides a kit, which utilizes the present direct detection methods. The kit includes instructions for performing the present methods utilizing an RT-PCR composition or an RT-composition to obtain either RT-PCR or RT reaction product, respectively, and amplifying the product. Alternatively, the instructions relate to direct detection of an RT-product without further amplification of it. Additionally, the kit may contain either an RT-PCR composition or RT composition, which results in an RT-PCR or RT reaction mixture, respectively, upon contact with the sample.

Detection of RT and RT-PCR Product

The instant invention is not limited as to the method of detection and may be used by any such method that detects the product of the RT or RT-PCR reaction.

RT Product Detection

Methods for directly detecting the cDNA product of an RT reaction are well known to one skilled in the art and make use of labels incorporated into or attached to the cDNA product. Signal generating labels that may be used are well known in the art and include, for example, fluorescent moieties, chemiluminescent moieties, particles, enzymes, radioactive tags, or light emitting moieties or molecules.

Fluorescent moieties are particularly useful, especially fluorescent dyes capable of attaching to nucleic acids and emitting a fluorescent signal. A variety of dyes are known in the art such as fluorescein, Texas Red, and rhodamine. Particularly useful are the mono reactive dyes Cy3 and Cy5, both available commercially (from, for example, Amersham Pharmacia Biotech, Arlington Heights, Ill.). A more sensitive way to specifically detect the labeled DNA is to hybridize the products against target DNA sequence molecules that are immobilized in a matrix, such as a nylon membrane or a glass slide. The signals after hybridization can then be scanned with a laser scanner with appropriate filtering to detect the specific dye used. This is well known in the art, especially in DNA microarray technology.

A label may be incorporated into the cDNA during its synthesis in the RT reaction, or it may be attached to the cDNA product after its synthesis. For example, the RT reaction can be carried out with labeled primers. One type of labeled primer has attached particles having a large number of signal generating molecules. Reverse transcription using a labeled nucleotide, such as dye-labeled UTP and/or CTP, incorporates a label into the transcribed nucleic acids. Alternatively, a post-synthesis coupling reaction can be used to detect the cDNA products.

Attaching labels to nucleic acids is well known to those of skill in the art and may be done by, for example, nick translation or end-labeling with, e.g. a labeled RNA or by treatment of the nucleic acid with kinase and subsequent attachment of a nucleic acid linker joining the sample nucleic acid to the label, e.g., a fluorophore. In another labeling method, the DNA products from the RT reaction are amplified by coupling to an in vitro transcription reaction. For example, the T7 promoter region is incorporated into the primer used for the RT reaction. A T7 in vitro transcription kit can then be used to generate a large amount of RNA to increase the detection sensitivity. The T7 in vitro transcriptional kit can be purchased from Ambion (2130 Woodward, Austin, Tex.) or other commercial sources.

RT-PCR Detection

Methods for RT-PCR product detection include gel electrophoresis separation and ethidium bromide staining, or detection of an incorporated fluorescent label or radiolabel in the product. Methods that do not require a separation step prior to detection of the amplified product may also be used. These methods are commonly referred to as Real-Time PCR or homogeneous detection. Most real time methods detect amplified product formation by monitoring changes in fluorescence during thermocycling. These methods include but are not limited to: TaqMan® dual labeled probes (Applied Biosystems, Foster City, Calif. 94404), Molecular Beacons (Tyagi S and Kramer FR (1996) Nat Biotechnol 14:303-308), and SYBR® Green dye (Molecular Probes, Inc Eugene, Oreg. 97402-0469). Some of these same homogeneous methods can be used for end point detection of amplified products as well. An example of this type of method is SYBR® Green dye dissociation curve analysis. In dissociation curve analysis a final slow ramp in temperature, generally about 60° C. to 90° C., combined with fluorescence monitoring can detect the melting point and thereby the presence of an amplified product (Ririe et al. (1997) Anal. Biochem. 245:154-60).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by J Sambrook, E F Fritsch and T Maniatis, *Molecular Cloning: A Laboratory Manual*, Cold Spring Harbor Laboratory Press, Cold Spring Harbor, N.Y., 1989, by T J Silhavy, M L Bennan, and L W Enquist, *Experiments with Gene Fusions*, Cold Spring Harbor Laboratory, Cold Spring Harbor, N.Y., 1984, and by F M Ausubel et al, *Current Protocols in Molecular Biology*, Greene Publishing Assoc. and Wiley-Interscience, NY, 1987. Materials and methods suitable for the maintenance and growth of bacterial cultures are also well known in the art. Techniques suitable for use in the following Examples may be found in *Manual of Methods for General Bacteriology*, P Gerhardt, R G E Murray, R N Costilow, E W Nester, Wash. Wood, N R Krieg and G B Phillips, eds, American Society for Microbiology, Washington, D.C., 1994, or by T D Brock in *Biotechnology: A Textbook of Industrial Microbiology*, 2$^{nd}$ Edition, Sinauer Associates, Inc, Sunderland, Mass., 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

The meaning of abbreviations used hereinbelow is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "pmole" means micromole(s), "g" means gram(s), "µg" means microgram(s), "mg" means milligram(s), "g" means the gravitation constant, "rpm" means revolutions per minute, "kb" means kilobase(s), "bp" means base pairs, "g" means the gravitation constant, "mU" means milliunit(s), "U" means unit(s), and "nm" means nanometer(s). "$OD_{650}$" means the optical density measured at 650 nm, "$OD_{260}/OD_{280}$" means the ratio of the optical density measured at 260 nm to the optical density measured at 280 nm.

The following enzymes and reagents were purchased from the following vendors:

Applied Biosystems (ABI), Foster City, Calif.: Multiscribe Reverse Transcriptase (Catalog #4311235); RNase Inhibitor (20 U/µL) (Catalog #N808-0119); GeneAmp 10×PCR Buffer II (100 mM Tris-HCl pH 8.3, 500 mM KCl) (Catalog #N808-0190); 25 mM $MgCl_2$ (Catalog #N808-0190)

Roche Applied Science, Indianapolis, Ind.: FastStart Taq DNA_Polymerase (Catalog #2032937); 25 mM $MgCl_2$ (Catalog #2032937)

Siqma Genosys, The Woodlands, Tex.: Oligonucleotides;

Invitrogen Life Technologies, Carlsbad, Calif.: 2% Double Comb Agarose E-gels (Cat #G6018-02); 2% Single Comb Agarose E-gels (Catalog #G5018-02); E-gel Low Range Quantitative DNA Ladder (Catalog #12373-031

Qiagen, Valencia, Calif.: RNase-Free DNase Set (Catalog #79254);

Sigma-Aldrich, St. Louis, Mo.: Bovin Serum Albumin (BSA) (Catalog #A3294); Dimethyl Sulfoxide (DMSO) (Catalog #D8418); Carbowax (Catalog #P5413); Trehalose (Catalog #T9531)

Becton Dickinson, Franklin Lakes, N.J.: Trypticase Soy Agar (TSA) (Catalog #221293); Trypticase Soy Broth (TSB) (Catalog #297811); Phosphate Buffer (Catalog #292786); Brain Heart Infusion culture media (BHI) (Catalog # 220837); Difco™ Fraser Broth Base (Catalog # 211767); Difco™ UVM Modified Listeria Enrichment Broth (Catalog # 222330); Difco™ PALCAM Medium Base (Catalog # 263620); Difco™ Oxford Medium Base (Catalog # 222530); Difco™ Fraser Broth Supplement (Catalog # 211742); Difco™ Oxford Antimicrobial Supplement (Catalog # 211763); Difco™ D/E Neutralizing broth (Catalog # B01256)

Oxoid, Ogdensburg, N.Y.; PALCAM Plus broth

The following test kits and reagents were purchased from the following vendors: Qiagen RNeasy Mini Kit (Qiagen, Valencia, Calif., Catalog #74106); DEPC (Diethyl pyrocarbonate) treated water (Fermentas, Hanover, Md., Catalog #R0601).

All oligonucleotide primers were synthesized by Sigma Genosys Company, The Woodlands, Tex. Polymerase Chain Reactions and Reverse Transcription Polymerase Chain Reactions were performed using the ABI PRISM 7000 Sequence Detection System (Applied Biosystems, Foster City, Calif.) and the PTC-255 Peltier Thermal Cycler (MJ Research Waltham, Mass.).

Genetic sequences were analyzed with Vector NTI Advance 9 (InforMax, Frederick, Md.). Sequences were downloaded from the National Center for Biotechnology Information (NCBI) (Bethesda, Md.). Primer sequences were aligned against the downloaded sequences using the Vector NTI software.

Example 1

Listeria innocua Cell Culture and cfu Determination

Listeria innocua (Strain CLIP 11262) was obtained from the American Type Culture Collection (ATCC #BM-680, Manassas, Va.). The Listeria innocua was hydrated with BHI culture medium. Cultures of Listeria innocua were spread and grown at 35° C. on TSA, then stored at 4° C.

A colony of Listeria innocua was removed from the TSA plate and placed in TSB. The tube containing the TSB was placed in the Incubator Shaker (Model G24, New Brunswick Scientific, Edison, N.J.) at 31° C. for 18 hours. For estimates of cell number, 1 mL of this culture was removed and placed in the Beckman DU-7500 Spectrophotometer (Beckman Coulter, Fullerton, Calif.). Absorbance was used to approximate cell concentration and was read at 600 nm. An absorbance of 1.0 was used as a reference and indicated approximately $1.0 \times 10^9$ cells/mL.

To determine cell number in stock solutions, diluted cell samples were prepared by transferring another 1 mL of the culture into 9 mL of phosphate buffer for a 1:10 dilution. This was repeated 8 times to obtain a serial dilution. 100 µL from the 1:100000, 1:1000000, and 1:10000000 dilutions were each plated onto TSA to obtain colony forming units (cfus) per mL of the original stock solution. The TSA plates were placed in a Gravity Convection Incubator (Precision Scientific Group, Chicago, Ill.) for 48 hours at 35° C. The plate that contained between 30 and 300 cfus was used to determine the original stock solution concentration by multiplying the number of cfus by the dilution factor, and dividing by 0.1 to account for the 100 µL placed on the plate. The value obtained represents cfus/mL.

Example 2

Detection of 16S rRNA Target Directly in Whole Cell Samples of Listeria innocua using Real Time RT-PCR In this example, a single step RT-PCR assay for the Listeria innocua 16S rRNA target sequence was performed on the bacterial cells with no prior lysis step.

An overnight culture of Listeria innocua cells ($3.6 \times 10^8$ cfus/mL) was prepared and diluted as indicated in Example 1. To prepare samples of cells for testing, 1 mL aliquots from the 1:1000 to 1:1000000000 dilutions were placed in Eppendorf Biopur tubes (Brinkmann Eppendorf, Westbury, N.Y., Catalog #22 60 004-4) that were then centrifuged on high (13,200 rpm) for 10 min in an Eppendorf 5415D Centrifuge (Brinkmann Eppendorf, Westbury, N.Y.). The phosphate buffer was removed from the samples.

A cell diluent was prepared by adding 5 µL RNase Inhibitor (100 U) to 45 µL of DEPC treated water. This 50 µL solution was added to each of the Biopur tubes containing a Listeria innocua cell pellet. Each tube was vortexed on a Mini Vortexer (VWR Scientific Products, West Chester, Pa.) on high (speed 10) for 15 sec. The tubes containing the diluted bacterial cells were immediately placed on ice.

A stock reaction mix (A) was prepared for RT-PCR, so that adding 45 µl to a final reaction volume of 50 µl resulted in the following final concentrations:
1) GeneAmp 1×PCR Buffer II of 10 mM Tris-HCl pH 8.3, 50 mM KCl
2) 2 mM $MgCl_2$
3) 200 µM Nucleotides
4) 24 µg BSA
5) 1:10,000 dilution of SYBR Green (10,000×; Catalog # S7567; Molecular Probes, Eugene, Oreg.) in DMSO (1% final concentration)
6) 600 nM forward primer, Lis-F (5'AGCTTGCTCTTC-CAAAGT 3'; SEQ ID NO:1) and 2 µM reverse primer, Lis-R (5'AAGCAGTTACTCTTATCCT 3'; SEQ ID NO:2). Primer sequences were from Somer and Kashi (2003 J. Food Prot. 66: 1658-1665).
7) 2.5 Units FastStart Taq DNA polymerase and 1.25 Units Multiscribe reverse transcriptase (Rt)
8) 1.86 mM Carbowax
9) 360.5 mM trehalose
10) 20 Units RNase Inhibitor For PCR reactions, a second reaction mix (B) was prepared as for the RT-PCR mix a, except that no Rt enzyme was added.

Reactions were performed in a MicroAmp Optical 96-well Reaction Plate (Applied Biosystems, Foster City, Calif., Catalog #N801-0560). For RT-PCR, 45 µL of reaction mix A was added to wells to determine the presence of both RNA and DNA. For PCR, 45 µL of reaction mix B was added to wells to determine the presence of only DNA.

A 5 µL sample of each diluted bacterial cell sample was added to the reaction mixes as listed in Tables 1 and 2. All reactions were replicated 3 times for each dilution.

A positive control sample of Listera RNA was prepared by extracting a sample containing $1.0 \times 10^8$ cfus using Qiagen's RNeasy Mini Kit. The extracted RNA was then DNase treated as described by the kit manufacturer and made up into a final volume of 50 µL of DEPC treated water. The RNA concentration (16 ng RNA/µl) was determined using the NanoDrop Spectrophotometer (NanoDrop Technologies, Rockland, Del.). This concentrated RNA was then diluted and 80 pg added per control reaction. This RNA control was used as a positive control for the RT-PCR reactions. Since the RNA was DNase treated, it was also used as a negative control for the PCR reaction. Additionally, 5 µL of DEPC treated water was used as a negative no target control.

The plate was sealed with ABI PRISM Optical Adhesive Covers (Applied Biosystems, Foster City, Calif., Catalog #4311971) and centrifuged in the Eppendorf Centrifuge 5804 (Brinkmann Eppendorf, Westbury, N.Y.). The samples were thermal cycled in the ABI PRISM 7000 using the following conditions:
50° C. 10 minutes (RT step);
95° C. 6 minutes (Taq activation step);
95° C. 30 seconds (denature step);
66° C. 1 minute (anneal and extend step);
Repeat denature and anneal steps 34 times;
66° C. 5 minutes;
Dissociation Protocol. (melt curves)

During thermocycling, CT values were determined for the formation of reaction product. Following the reactions, product formation was analyzed using both melt-curve analysis and separation by agarose gel electrophoresis. Samples were run on 2% Single Comb Agarose E-gels in the E-gel base (Catalog #G5100-01, Invitrogen Life Technologies, Carlsbad, Calif.) that was plugged into a Low Voltage Power Supply (Model 250EX, Whatman Biometra, Germany) and run at 60 Volts for 20 min. The E-gel image was captured on the Kodak Image Station 440CF (Kodak Digital Science, Rochester, N.Y.) and then viewed to determine the presence or absence of a correct size RT-PCR product (402 bp).

Figure 1B:
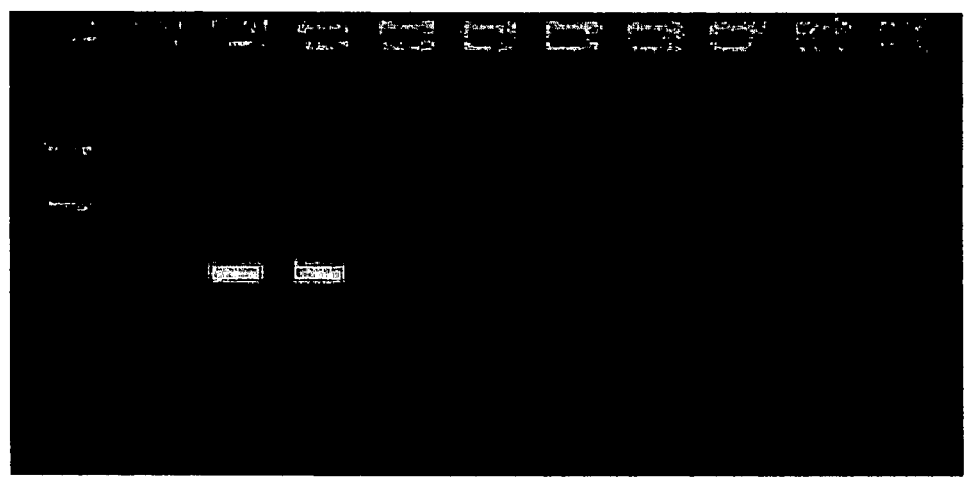

The reaction products from the RT-PCR and PCR reactions of the bacterial cell samples are shown in FIG. 1 alongside the Low Range Quantitative DNA Ladder (Bands from top to bottom are 2000 bp, 800 bp, 400 bp, 200 bp, and 100 bp). The 402 bp predicted reaction product was amplified in both RT-PCR (seen in lanes 2 to 5) and PCR (seen in lanes 12 and 13, and very light in lane 14) reactions from bacterial cell samples, and the control RT-PCR reaction with purified RNA (lane 1).

The formation of reaction products was also seen in the ABI PRISM 7000 dissociation data. In the dissociation protocol, the temperature is raised causing the amplified DNA strands to separate which results in changing fluorescence. The derivative is taken of this rate of change in fluoescence, which produces a peak over the temperature region where the DNA strands melt apart and which is related to the amount of amplified DNA present. Derivative peak values are used as a qualitative measure for the presence of an amplified product. Derivative values in excess of 300 were considered a positive indication of product formation as a result of the RT-PCR or PCR. The high derivative values in Tables 1 and 2 for samples 2 to 5, and 12 to 14 indicated that the amplified DNA product was present, as in the sample 1 control.

TABLE 1

RT-PCR Sample Analysis: Melt-Curve Derivatives and CTs

| Sample | Amount/reaction | Mean Derivative peak | Mean CT value |
|---|---|---|---|
| 1 | 80 pg RNA | 827.1 | 13.72 |
| 2 | $3.6 \times 10^4$ Cells | 1087.9 | 18.47 |
| 3 | $3.6 \times 10^3$ Cells | 1201.5 | 21.69 |
| 4 | $3.6 \times 10^2$ Cells | 1039.9 | 25.20 |
| 5 | $3.6 \times 10^1$ Cells | 960.0 | 27.01 |
| 6 | $3.6 \times 10^0$ Cells | 143.6 | 31.93 |
| 7 | $3.6 \times 10^{-1}$ Cells | 56.9 | 32.35 |
| 8 | $3.6 \times 10^{-2}$ Cells | 150.7 | 31.67 |
| 9 | 0 Cells | 40.6 | 32.01 |
| 10 | water | 52.6 | 32.64 |

TABLE 2

PCR Sample Analysis: Melt-Curve Derivatives and CTs

| Sample | Amount/Reaction | Mean Derivative peak | Mean CT value |
|---|---|---|---|
| 11 | 80 pg RNA | 69.5 | 33.95 |
| 12 | $3.6 \times 10^4$ Cells | 1162.9 | 23.18 |
| 13 | $3.6 \times 10^3$ Cells | 1228.6 | 26.24 |
| 14 | $3.6 \times 10^2$ Cells | 325.9 | 31.39 |
| 15 | $3.6 \times 10^1$ Cells | 122.4 | 33.20 |
| 16 | $3.6 \times 10^0$ Cells | 67.8 | 33.37 |
| 17 | $3.6 \times 10^{-1}$ Cells | 84.4 | 33.30 |
| 18 | $3.6 \times 10^{-2}$ Cells | 64.5 | 33.47 |
| 19 | 0 Cells | 216.2 | 32.05 |
| 20 | water | 77.5 | 34.11 |

Cycle Threshold (CT) data from the ABI PRISM 7000 is inversely related to the abundance of target. From the no cell and water samples it was determined that CT values of 32-34 were background levels. The CT values of 27 and below shown for samples 2 to 5, 12 and 13 in Tables 1 and 2 indicated successful amplification reactions. The CT value of 31.39 for sample 14 was also just below background. Product formation was directly related to the number of cells added to the reaction. Comparing samples 12 vs 2 and 13 vs 3 showed a difference in CT values of approximately 5 for the same number of cells in PCR vs RT-PCR reactions. The lower limit of detection in the RT-PCR reaction was $3.6 \times 10^1$ cells while the lower limit of detection in the PCR reaction was $3.6 \times 10^2$ cells. These results demonstrate that without RNA purification or prior cell lysis, bacterial cell RNA was readily available for RT-PCR detection.

Example 3

Reproducibility of 16S rRNA Target Detection in Whole Cell Samples of Listeria innocua using Real Time RT-PCR Listeria innocua cultures were grown overnight and processed as in Example 1. Cell samples were tested under the same exact conditions as in Example 2, in two additional experiments (different days).

Figure 2:
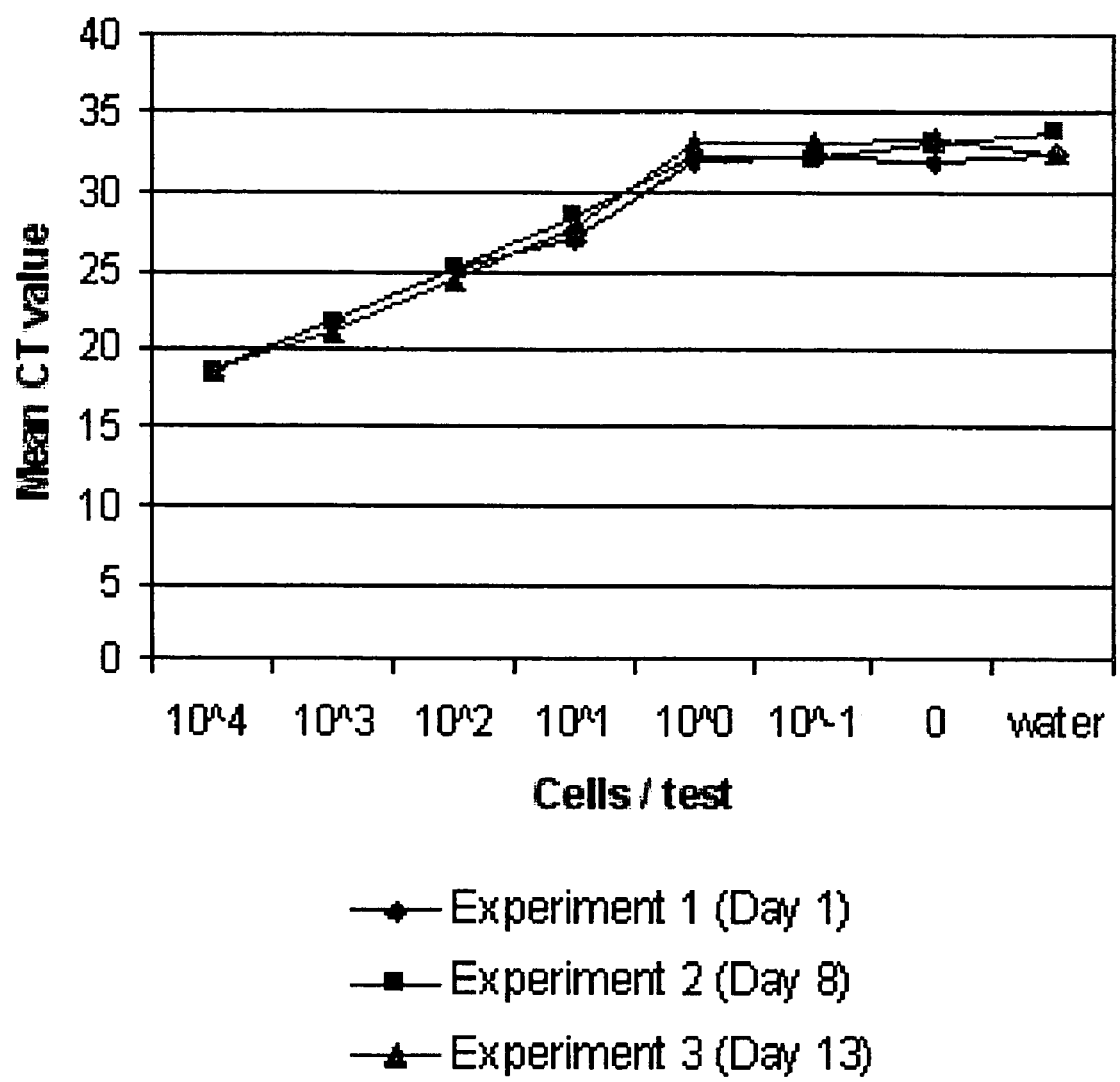
Figure 3:
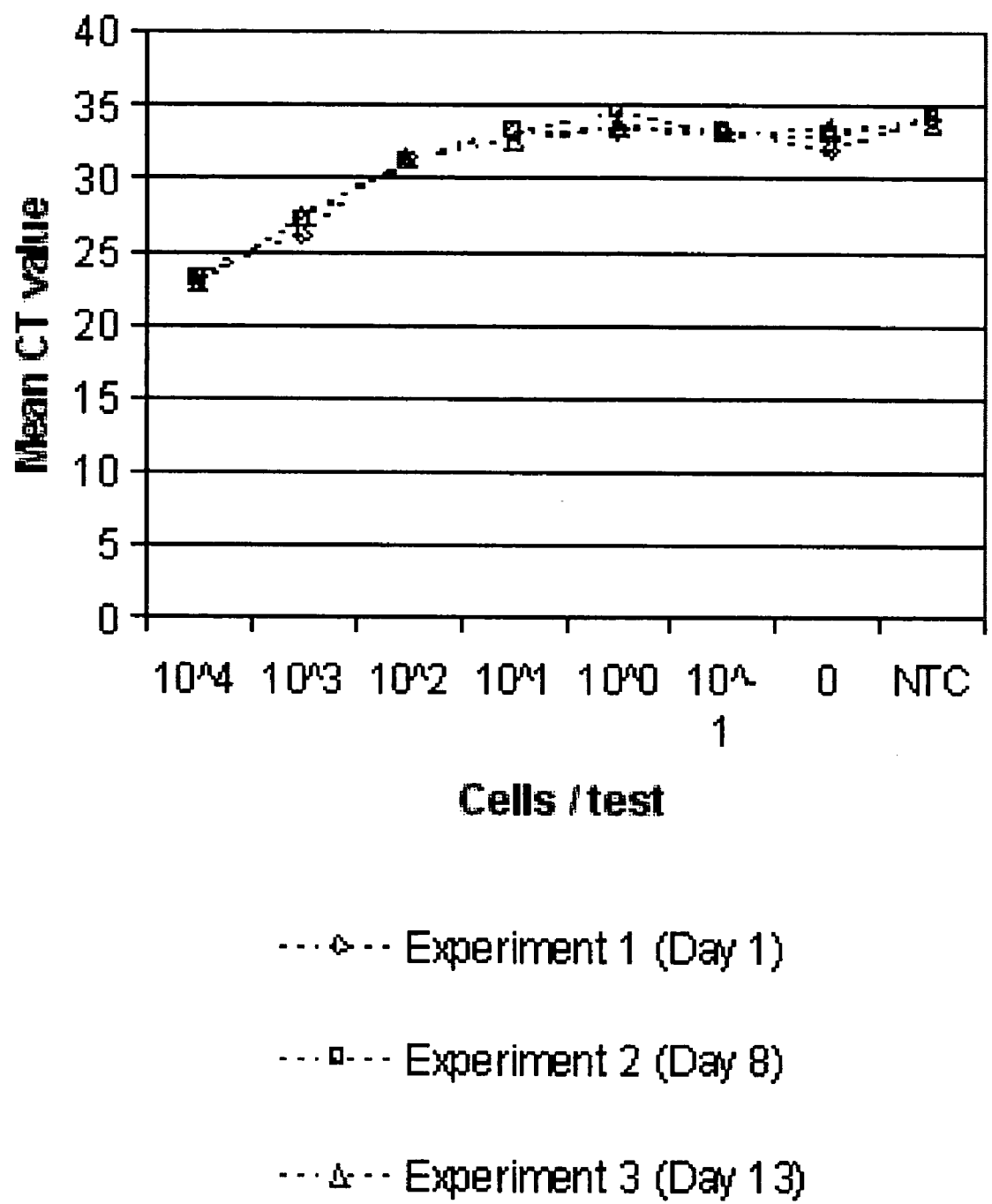
FIG. 3 shows a comparison of CT values for three different PCR reaction sets using bacterial cell samples.
Figure 4:
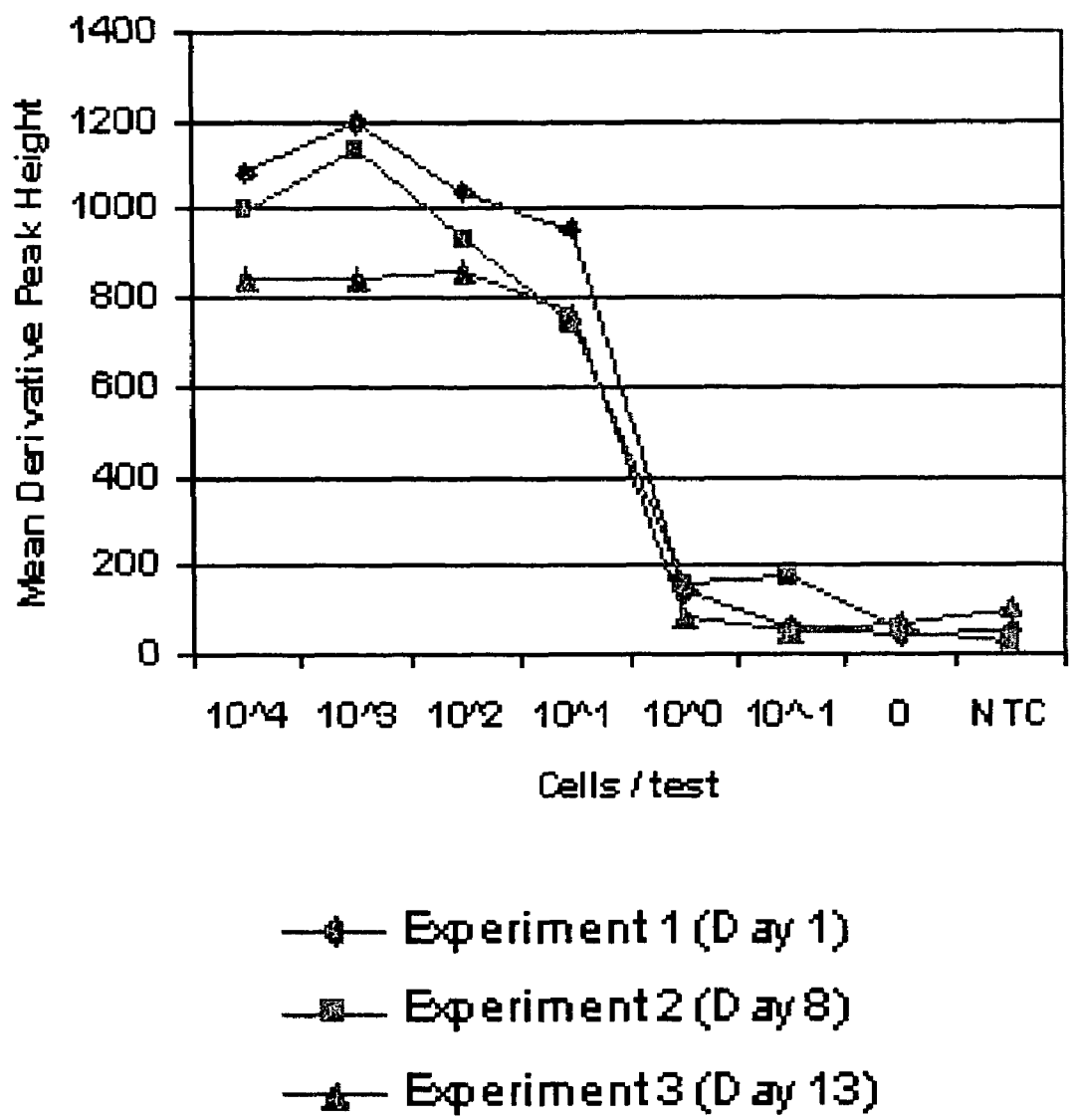
FIG. 4 shows a comparison of derivative peak values for three different RT-PCR reaction sets using bacterial cell samples.
Figure 5:
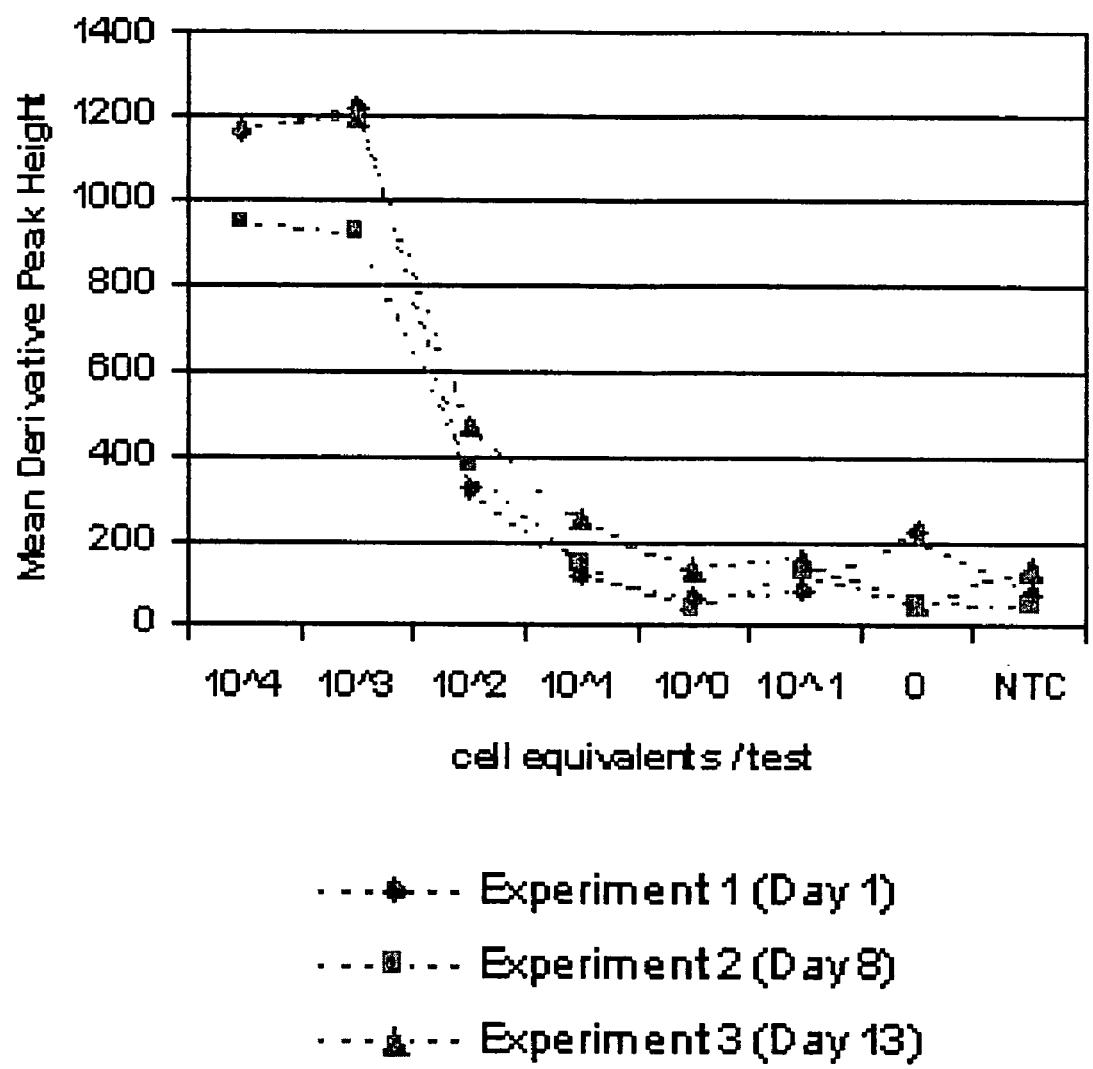
FIG. 5 shows a comparison of derivative peak values for three different PCR reaction sets using bacterial cell samples.

Plots of the CT values for the RT-PCR and PCR reactions from experiments run on Day 1, 8 and 13 are shown in FIGS. 2 and 3. The number of cells per reaction from experiments run on Day 1 ranged from $3.6 \times 10^4$ to $3.6 \times 10^{-1}$, $3.2 \times 10^4$ to $3.2 \times 10^1$ on Day 8, and $7.5 \times 10^4$ to $7.5 \times 10^{-1}$ on Day 13. The plots show that the CT values were closely reproduced among the different experiments. The derivative peak data for the same reactions are shown in FIGS. 4 and 5. The plots of these data also showed that the data were reproduced. Both types of data indicated that RNA was directly detectable from Listeria bacterial cells without RNA extraction or prior cell lysis.

Example 4

Pretreatment for Direct Detection of 16S rRNA Target in Whole Cell Samples of Listeria innocua using Real Time RT-PCR Listeria innocua cells were prepared as in Example 1. Cell samples were centrifuged and resuspended in water containing RNase inhibitor, as in Example 2. In this example, 3 sets of cell samples ranging in concentration from $10^5$ to $10^0$ cells per 50 µL were prepared. One set was held on ice prior to testing, as a no pretreatment control. The second set of samples was placed in a Heat Block (VWR Scientific Products, West Chester, Pa.) at 50° C. for 5 min and then held on ice before testing. The third sample set was placed in a Heat Block at 95° C. for 1 min and then placed on ice. This set was used to evaluate the effect of a high temperature heat treatment of the cells. RT-PCR reagent reaction mix (with Rt) and the PCR reagent reaction mix (without Rt) were prepared as in Example 2. 5 µL from each test set was added to the RT-PCR reagent reaction mix, and an additional 5 µL from each test set was added to the PCR reagent reaction mix. The RT-PCR and PCR reactions were performed in triplicate. The test reactions where then thermal cycled as in Example 2 in an ABI PRISM 7000.

The melt-curve derivative peak data for this experiment are listed in the following Tables 3 and 4. The results shown in Tables 3 and 4 demonstrated that cell pretreatment did not adversely affect the RT-PCR or PCR assays. The derivative peak values showed product amplification in the pretreated samples as well as the control. As in Example 2, product formation was inferred from derivative peak values greater than 300. Product was detected in the samples with $2.52 \times 10^1$ cells in the RT-PCR reaction while product was detected in the samples with $2.52 \times 10^2$ cells in the PCR reaction, which indicated as in Example 2 that bacterial cell RNA was readily available for RT-PCR detection.

TABLE 3

Pretreatment effects on RT-PCR Derivative peak values

| Cells/test | No Pretreatment Control Mean Der. Peak | 5 min @ 50° C. Mean Der. Peak | 1 min @ 95° C. Mean Der. Peak |
|---|---|---|---|
| $2.52 \times 10^4$ | 1013.4 | 1209.2 | 1357.7 |
| $2.52 \times 10^3$ | 1161.2 | 1305.8 | 1476.8 |
| $2.52 \times 10^2$ | 1126.7 | 1041.2 | 1242.1 |
| $2.52 \times 10^1$ | 688.2 | 787.5 | 768.4 |
| $2.52 \times 10^0$ | 30.4 | 190.8 | 259.8 |
| $2.52 \times 10^{-1}$ | 23.1 | 74.8 | 32.3 |
| 0 | 30.0 | 30.5 | 50.4 |

TABLE 4

Pretreatment effects on PCR Derivative peak values

| Cells/test | No Pretreatment Control Mean Der. Peak | 5 min @ 50° C. Mean Der. Peak | 1 min @ 95° C. Mean Der. Peak |
|---|---|---|---|
| $2.52 \times 10^4$ | 1474.1 | 1501.1 | 1474.6 |
| $2.52 \times 10^3$ | 1312.0 | 1425.3 | 1569.0 |
| $2.52 \times 10^2$ | 552.6 | 1225.4 | 1095.1 |
| $2.52 \times 10^1$ | 297.9 | 193.2 | 117.2 |
| $2.52 \times 10^0$ | 64.7 | 94.9 | 56.1 |
| $2.52 \times 10^{-1}$ | 108.1 | 189.2 | 178.6 |
| 0 | 106.9 | 106.8 | 149.9 |

Example 5

Comparison of Direct 16S rRNA target Detection with Isolated RNA target Detection in RT-PCR

*Listeria innocua* bacterial cells were prepared and diluted as in Examples 1 and 2. The RNA from these cells was then isolated using the Qiagen RNeasy Mini Kit (RNeasy Mini Handbook pages 28, 56-60) RNA extraction kit. Specifically, 1 mL from each cell sample dilution was centrifuged for 10 min (13,200 rpms) in the Eppendorf 5415D Centrifuge (Brinkmann Eppendorf, Westbury, N.Y.). The phosphate buffer was removed and the bacterial cells were then lysed per the Qiagen protocol (RNeasy Mini Handbook) for 10 min. The lysed samples were then added to the kit silica-gel-based membrane in the column to bind the RNA. The optional DNase treatment was not performed. 50 μL of water were added to the column to elute the RNA from the membrane. The eluant was reapplied and eluted from the membrane to concentrate the RNA in the solution. This recovered RNA was then placed on ice until testing.

For comparison, two additional series of diluted bacterial cell samples were prepared in water and RNase inhibitor, and pretreated as in Example 4 (5 min at 50° C. or 1 min at 95° C.). The isolated RNA, extracted by the Qiagen kit, and the heat-treated cells were analyzed in RT-PCR and PCR reactions as detailed in Example 2.

The RT-PCR and PCR products obtained from these reactions as measured by CT values and melt-curve derivative values are reported respectively in Tables 5, 6 and 7, 8. No advantage was found for purified RNA over the direct bacterial cell detection method in either the RT-PCR or PCR responses (CT or melt-curve derivative values). In fact, the heat treated bacterial cell samples had slightly better (lower) RT-PCR CT values than the purified RNA, especially those heated for 1 min at 95° C.

TABLE 5

Comparison of RT-PCR CT values between Isolated RNA and Direct Cell Detection using *Listeria innocua* cells

| Cells/test | Extracted RNA Mean CT | 5 min @ 50° C. Mean CT | 1 min @ 95° C. Mean CT |
|---|---|---|---|
| $6.5 \times 10^4$ | 19.09 | 18.70 | 17.57 |
| $6.5 \times 10^3$ | 23.65 | 22.52 | 21.60 |
| $6.5 \times 10^2$ | 25.62 | 25.66 | 25.15 |
| $6.5 \times 10^1$ | 30.59 | 28.75 | 27.21 |
| $6.5 \times 10^0$ | 32.22 | 32.50 | 31.96 |
| $6.5 \times 10^{-1}$ | 31.85 | 33.82 | 31.01 |
| 0 | 34.05 | 33.55 | 31.95 |

TABLE 6

Comparison of PCR CT values between Isolated RNA and Direct Cell Detection using *Listeria innocua* cells.

| Cells/test | Extracted RNA Mean CT | 5 min @ 50° C. Mean CT | 1 min @ 95° C. Mean CT |
|---|---|---|---|
| $6.5 \times 10^4$ | 23.02 | 22.12 | 23.03 |
| $6.5 \times 10^3$ | 26.98 | 25.92 | 26.56 |
| $6.5 \times 10^2$ | 29.88 | 29.14 | 30.86 |
| $6.5 \times 10^1$ | 33.08 | 31.63 | 31.87 |
| $6.5 \times 10^0$ | 34.20 | 33.45 | 34.20 |
| $6.5 \times 10^{-1}$ | 33.70 | 33.46 | 32.03 |
| 0 | 33.96 | 32.62 | 34.90 |

TABLE 7

Comparison of RT-PCR derivative peak values between Isolated RNA and Direct Cell Detection using *Listeria innocua* cells

| Cells/test | Extracted RNA Mean Der. Peak | 5 min @ 50° C. Mean Der. Peak | 1 min @ 95° C. Mean Der. Peak |
|---|---|---|---|
| $6.5 \times 10^4$ | 877.9 | 1206.7 | 1309.4 |
| $6.5 \times 10^3$ | 1070.9 | 1188.0 | 1405.3 |
| $6.5 \times 10^2$ | 1125.1 | 1091.4 | 1212.8 |
| $6.5 \times 10^1$ | 640.2 | 933.9 | 994.0 |
| $6.5 \times 10^0$ | 292.8 | 230.2 | 94.9 |
| $6.5 \times 10^{-1}$ | 227.5 | 81.2 | 125.8 |
| 0 | 32.8 | 126.6 | 112.1 |

TABLE 8

Comparison of PCR derivative peak values between Isolated RNA and Direct Cell Detection using *Listeria innocua* cells

| Cells/test | Extracted RNA Mean Der. Peak | 5 min @ 50° C. Mean Der. Peak | 1 min @ 95° C. Mean Der. Peak |
|---|---|---|---|
| $6.5 \times 10^4$ | 1449.8 | 1531.7 | 1240.9 |
| $6.5 \times 10^3$ | 1341.3 | 1455.7 | 1451.0 |
| $6.5 \times 10^2$ | 936.7 | 1166.7 | 713.1 |
| $6.5 \times 10^1$ | 195.5 | 434.2 | 417.5 |
| $6.5 \times 10^0$ | 90.6 | 179.6 | 113.6 |
| $6.5 \times 10^{-1}$ | 120.2 | 169.7 | 205.0 |
| 0 | 96.0 | 127.3 | 41.3 |

Example 6

RNase Inhibitor Effects on Heat Pretreated Cell Samples for Direct Target RNA Detection

*Listeria innocua* cells were grown as in Example 1 and diluted 1:10000 in phosphate buffer. Fourteen 1 mL aliquots of the diluted cells were removed and prepared as in Example 2 with half of the samples being resuspended in 50 µL of a 45:5 µL of water:RNase Inhibitor (100 U) mix, and the other half being resuspended in 50 µL of water only; no RNase inhibitor was added. All samples were vortexed.

Prior to RT-PCR assays, one tube from each sample set (with RNase inhibitor and without RNase inhibitor) was held on ice as a time zero positive control. The remaining tubes were placed in a 50° C. heat block, as in Example 4. One tube from each treatment condition was removed from the heat block and placed on ice at each of the following time points: 1 min, 2 min, 5 min, 10 min, 15 min, and 20 min.

Aliquots of 45 µL of RT-PCR reaction mix, as described in Example 2, were placed in a 96-well plate. From each of the 50° C. heat treated samples, and controls, three samples of 5 µL were removed, added to 45 µL CR reaction mix, and the reaction was thermocycled as described in Example 2. The CT values for these reactions are shown in Table 9 and the melt-curve derivative peak values in Table 10.

As shown in Table 9, after the 5 min incubation at 50° C., a divergence in CT values between the sample with RNase inhibitor and the sample that lacked RNase inhibitor was seen. The smaller CT value for the sample with RNase inhibitor indicated the presence of more available target RNA for RT-PCR. Thus a 50° C. treatment for 5 min or more in the presence of RNase inhibitor increased the availability of bacterial cell RNA in the RT-PCT assay.

TABLE 9

RNase inhibitor effects with varying time of 50° C. pretreatment on RT-PCR assay CT values

| Time at 50° C. prior to RT-PCR | With RNase inhibitor Mean CT | Without RNase inhibitor Mean CT |
|---|---|---|
| 0 | 24.96 | 25.35 |
| 1 | 23.86 | 24.36 |
| 2 | 24.16 | 24.50 |
| 5 | 21.99 | 25.16 |
| 10 | 21.84 | 23.05 |
| 15 | 21.78 | 24.77 |
| 20 | 21.60 | 24.33 |

TABLE 10

RNase inhibitor effects with varying time of 50° C. pretreatment on RT-PCR assay derivative peak values

| Time at 50° C. prior to RT-PCR | With RNase Inhibitor Mean Der. Peak | Without RNase inhibitor Mean Der. Peak |
|---|---|---|
| 0 | 904.0 | 940.3 |
| 1 | 920.1 | 909.6 |
| 2 | 907.0 | 901.8 |
| 5 | 951.3 | 809.9 |
| 10 | 927.2 | 1037.2 |
| 15 | 973.9 | 882.3 |
| 20 | 911.3 | 926.6 |

Bacterial cell samples with and without RNase inhibitor as described above were heated at 95° C. for the same time periods as above and then assayed by RT-PCR as above. The RT-PCR results in CT values and melt-curve derivative peak values for these treatments are reported respectively in Tables 11 and 12.

TABLE 11

RNase inhibitor effects with varying time of 95° C. pretreatment on RT-PCR assay CT values

| Time at 95° C. prior to RT-PCR | With RNase Inhibitor Mean CT | Without RNase inhibitor Mean CT |
|---|---|---|
| 0 | 23.1 | 24.3 |
| 1 | 22.4 | 21.8 |
| 2 | 22.0 | 22.1 |
| 5 | 21.7 | 23.3 |
| 10 | 22.6 | 24.4 |
| 15 | 22.9 | 27.1 |
| 20 | 23.3 | 28.1 |

TABLE 12

RNase inhibitor effects with varying time of 95° C. pretreatment on RT-PCR assay derivative peak values

| Time at 95° C. prior to RT-PCR | With RNase Inhibitor Mean Der. peak | Without RNase inhibitor Mean Der. peak |
|---|---|---|
| 0 | 895.6 | 946.7 |
| 1 | 891.7 | 943.9 |
| 2 | 897.5 | 926.1 |
| 5 | 925.4 | 783.9 |
| 10 | 994.7 | 984.4 |
| 15 | 949.4 | 782.4 |
| 20 | 860.9 | 796.3 |

The CT values indicated that heat treatment at 95° C. without RNase inhibitor for 1 to 5 min increased availability of RNA template for the RT-PCR assay (lower CT values than control). With RNase inhibitor, a 95° C. treatment for 1 to 10 minutes increased availability of RNA template for the RT-PCR assay.

Although the RT-PCR response over time with both 50° C. and 95° C. treatments indicated some RNA degradation over time, RNA amplification occurred at all time points tested under both treatment conditions as indicated by the derivative response. This result demonstrated that RNase inhibitor is not necessary for RT-PCR direct bacterial cell detection, but RNase inhibitor can enhance the response when it is present. Thus, RNA was detected under both heat treatments with and without RNase inhibitor, but more RNA was available when RNase inhibitor was present.

Example 7

Detection of 16S rRNA Target Directly in whole Cell Lysates of *Listeria innocua* using Real Time RT-PCR Strain and Media

*Listeria innocua* cells were grown at 37° C. in Demi-Fraser medium plus 0.3% glucose (Cat. # CM0153, Oxoid, Ltd., Ogdensburg, N.Y.). Plate counts were performed on BHI agar plates (Cat. # B1010, Teknova, Inc., Hollister, Calif.).

Preparation of Whole Cell Lysates by Ambion Lysis Method 10 ml of Demi-Fraser plus 0.3% glucose medium was inoculated with *Listeria innocua* and incubated overnight at 37° C. 100 µl of overnight culture were transferred into fresh medium and the $OD_{650}$ was measured using an Ultra Spec 3000 (Pharmacia Biotech, Piscataway, N.J.). The culture was incubated at 37° C. until the $OD_{650}$ reached 0.5 (mid-log phase). 33 µl of culture were transferred into 967 µl of ice cold PBS (Ambion Cells to cDNA kit, Cat. # 1722, Ambion, Inc., Austin, Tex.). Cells were pelleted by centrifugation for 1 minute at 13,000 rpm in a Heraeus Biofuge Pico (Kendro Laboratory Products, Asheville, N.C.) and then resuspended in 100 µl of ice cold PBS. Cells were diluted 1:10 in ice cold PBS and then serial 1:10 dilutions were made in Ambion Lysis Buffer (Ambion Cells to cDNA kit, Cat. # 1722, Ambion, Inc., Austin, Tex.) to a final concentration of approximately $10^2$ cells/ml.

Another set of serial 1:10 dilutions was made in PBS to a final concentration of approximately $10^2$ cells/ml for performing plate counts. From dilutions at approximately $10^3$ and $10^2$ cells/ml, 100 µl were spread on BHI agar plates. Plates were incubated at 37° C. for 18 hrs and the number of colonies per plate was counted to determine cfu per each dilution.

From each dilution in Ambion Lysis Buffer containing approximately $10^5$ cells/ml to $10^2$ cells/ml, 90 µl of diluted cells were transferred to 0.5 ml thin-walled PCR tubes. Cells were incubated for 10 min at 75° C. in the GeneAmp PCR System 9700 (PE Applied Biosystems, Foster City, Calif.). The resulting cell sample lysate was immediately used in RT-PCR reactions described below.

Preparation of Whole Cell Lysates by BAX Lysis Method

Cultures were grown and prepared as described above except that pelleted cells were diluted first by 1:5 instead of 1:10, and then diluted serially by 1:10 as above to a final concentration of approximately $2 \times 10^2$ cells/ml. Above plate counts were used for both lysis methods as the same culture was used to prepare both sets of dilutions and lysates. From each dilution in PBS containing approximately $2 \times 10^6$ cells/ml to $2 \times 10^3$ cells/ml, 5 µl of diluted cells were added to 100 µl of BAX Lysis Buffer (BAX System PCR assay for screening Genus Listeria, Cat. # 17710610, DuPont Qualicon, Wilmington, Del.) in 0.5 ml thin-walled PCR tubes. Cells were incubated for 1 hr at 55° C. and then 10 min at 95° C. in the GeneAmp PCR System 9700 (PE Applied Biosystems, Foster City, Calif.). The resulting cell sample lysate was immediately used in RT-PCR reactions below.

RT-PCR

Real time Reverse Transcription-PCR (RT-PCR) was performed on a Sequence Detection System (SDS) instrument (Applied Biosystems, Foster City, Calif./USA, Model 7900). Real Time primers and probe were designed using Primer Express v 2.0 software (AppliedBiosystems, Foster City, Calif./USA) using the standard settings. 20 µl reactions were set up as follows both with and without Reverse Transcriptase (+ or −Rt): 10 µl TaqMan Universal PCR 2× Master Mix (AppliedBiosystems, Foster City, Calif./USA, #4324018; contains AmpliTaq Gold® DNA polymerase), 0.4 µl RNase Inhibitor (AppliedBiosystems, Foster City, Calif./USA, #N808-0119, 20 U/ul), 0.01 µl MultiScribe Reverse Transcriptase (AppliedBiosystems, Foster City, Calif./USA, #4311235), 0.1 ul 16S-373F 100 µM primer (Sigma Genosys, Woodlands, Tex./USA, 5' TCCGCAATGGACGAAAGTCT: SEQ ID NO:3), 0.2 µl 16S-436R 100 µM primer (Sigma Genosys, Woodlands, Tex./USA, 5' TTACGATCCGAAAACCTTCTTCA: SEQ ID NO:4), 0.05 µl 16S-394T 100 µM TaqMan TAMRA Probe (AppliedBiosystems, Foster City, Calif./USA, #450025,6 FAM-ACGGAGCAACGC-CGCGTG: SEQ ID NO:5), 7.24 µl Molecular Biology Grade water (Eppendorf AG, Hamburg/Germany #0032006.302), and 2 µl sample lysate. All reactions were run in triplicate. Reactions were run without Rt to determine the detectable amount of DNA present in the lysates. Only the two highest concentration lysates were run without Rt.

Reactions were thermal cycled as follows: 50° C. for 10 min, 95° C. for 10 min, followed by 40 cycles of 95° C. for 15 sec+60° C. for 1 min. Prior to thermocycling the 6-FAM reporter dye fluorescence on the 5' end of the TaqMan® probe is effectively quenched by the 3' TAMRA dye due to its close proximity. During thermocycling the probe binds to one strand of the amplified product upstream of one of the PCR primer binding sites. As the PCR primer is extended by AmpliTaq Gold®, it cleaves the probe via its 5'-3' exonuclease activity. Cleavage of the probe separates the reporter and quencher dyes and results in an increase in reporter dye fluorescence. The reporter dye fluorescence is collected by the SDS instrument. The 7900 SDS instrument compares the increase in fluorescence to the background fluorescence from the first few thermal cycles where the majority of the reporter fluorescence is quenched. The software then determines the CT value at a point significantly above background fluorescence for all samples.

The CT values shown in Table 13 follow a pattern that would be predicted for detection of purified target RNA and DNA. There was a dose response or increase in CT as the amount of target RNA or DNA was decreased across the 1:10 dilution series. This result means that as the samples were diluted it took increasingly longer for the reporter fluorescence to reach the threshold determined by the instrument. Thus the direct assay of the lysed *Listeria innocua* bacterial cell samples showed detection of target RNA by RT-PCR in a pattern comparable to detection expected from purified nucleic acid samples.

The lower CT values seen in the Ambion lysis data indicate that this lysis method was more efficient at providing RNA template for amplification compared to the BAX lysis method.

TABLE 13

Lysate Comparison CT Values

| Cfu/test | Ambion (+) Rt Mean CT | BAX (+) Rt Mean CT | Ambion (−) Rt Mean CT | BAX (−) Rt Mean CT |
|---|---|---|---|---|
| $2 \times 10^2$ | 18.95 | 25.74 | 25.57 | 33.48 |
| $2 \times 10^1$ | 22.78 | 29.39 | 29.21 | 36.95 |
| $2 \times 10^0$ | 26.74 | 32.73 | | |
| $2 \times 10^{-1}$ | 28.64 | 34.61 | | |
| 0 | >40 | >40 | >40 | >40 |

The lower CT values observed in the (+) Rt reactions compared to the (−) Rt reactions indicated that high copy number RNA was detected in these reactions. Since a doubling of amplification products occurs during each cycle of a PCR reaction, the difference in CT values or ΔCT between the (+) and (−) Rt reactions can be related by the equation: $2^{-\Delta CT}$ (ΔCt from Applied Biosystems User Bulletin #2, December 1997). This equation was used to calculate the differences in number of template RNA copies in the (+) Rt reactions relative to the number of template DNA copies in the (−) Rt reactions. The values are shown in Table 14. These calculated values indicated that there was approximately 100-200 fold more copies of template RNA than of template DNA in the lysed cell samples.

TABLE 14

Quantitation of 16s rRNA Copies Detected Realtive to DNA

| cfu/test | $\Delta CT =$ (+)Rt − (−)Rt Ambion | $2^{\wedge} - \Delta CT$ Ambion | $\Delta CT =$ (+)Rt − (−)Rt BAX | $2^{\wedge} - \Delta CT$ BAX |
|---|---|---|---|---|
| $2 \times 10^2$ | −6.61 | 97.8 | −7.74 | 213.5 |
| $2 \times 10^1$ | −6.43 | 86.3 | −7.55 | 187.7 |

This example showed that the lysis procedures described here which do not call for RNA or DNA purification generate levels of target RNA that are detectable by RT-PCR.

Example 8

Detection of 16S rRNA Target Directly in Whole Cell Lysates of *Listeria monocytogenes* using Real Time RT-PCR Strain and Media Cells of *Listeria monocytogenes* strain DD1288 were grown at 37° C. in Demi-Fraser medium plus 0.3% glucose (Cat. #CM0153, Oxoid, Ltd., Ogdensburg, N.Y.). DD1288 is a strain obtained from DuPont Qualicon (Wilmington, Del.) that had been isolated from cooked turkey and identified as a strain of *L. monocytogenes* by its pattern of growth on differential agars and its characteristics in biochemical tests as described in the USDA/FSIS Microbiology Laboratory Guidebook (Cook, L. V. 2002, 3rd ed., revision 3, USDA/FSIS; http://www.fsis.usda.gov/Frame/FrameRedirect.asp?main=op/ophs/ophshome.htm). Other *L. monocytogenes* strains may be used to demonstrate the detection of 16S rRNA target directly in whole cell lysates, as described in this example. Plate counts, as described in Example 1, were performed on BHI agar plates (Cat. # B1010, Teknova, Inc., Hollister, Calif.).

Preparation of Whole Cell Lysates by Ambion Lysis Method

*Listeria monocytogenes* cells were grown, harvested, diluted, and plate counts taken as described in Example 7 for the Ambion lysis method. From each dilution in Ambion Lysis Buffer containing approximately $10^5$ cells/ml to $10^2$ cells/ml, 90 μl of diluted cells was transferred to 0.5 ml thin-walled PCR tubes. Cells were incubated for 10 min at 75° C. in a GeneAmp PCR System 9700 (PE Applied Biosystems, Foster City, Calif.).

RT-PCR

Real time Reverse Transcription-PCR (RT-PCR) was performed as described in Example 7 using 2 μl of *Listeria monocytogenes* cell lysate sample per reaction. All reactions were run in triplicate.

Reactions were thermal cycled as in Example 7 and the CT values are shown in Table 15. As in Example 7, the CT values followed a pattern that would be predicted for detection of purified target RNA and DNA, and so demonstrated that the direct assay of lysed cells was effective. Without purification, the 16S rRNA and 16S rDNA were available to function as template in RT-PCR and PCR assays. The data showed a characteristic increase in CT value as the level of lysate dilution was increased giving lower cfu in the reaction. Reactions including reverse transcriptase contained significantly more target DNA copies of the 16S sequence to serve as template for PCR as shown by the calculated $2^{-\Delta CT}$ values given in Table 16.

TABLE 15

Ambion Lysates Ct Values

| Cfu/test | Ambion (+) Rt Mean Ct | Ambion (−) Rt Mean Ct |
|---|---|---|
| $1 \times 10^3$ | 18.66 | 25.08 |
| $1 \times 10^2$ | 21.18 | 27.83 |
| $1 \times 10^1$ | 24.19 | 31.14 |
| $1 \times 10^0$ | 28.19 | 34.94 |
| 0 | >40 | >40 |

TABLE 16

Ambion Lysate Relative Quantitation

| Cfu/test | $\Delta Ct =$ (+)Rt − (−)Rt Ambion | $2^{\wedge -\Delta Ct}$ Ambion |
|---|---|---|
| $1 \times 10^3$ | −6.42 | 85.81 |
| $1 \times 10^2$ | −6.65 | 100.21 |
| $1 \times 10^1$ | −6.96 | 124.10 |
| $1 \times 10^0$ | −6.75 | 107.81 |

Example 9

Detection of 16S rRNA Target Directly in Whole Cell Lysates of *Escherichia coli* using Real time RT-PCR Strain and Media

*E. coli* ATCC 25922 was obtained from the American Type Culture Collection (Manassas, Va.). Cells were grown at 37° C. in BHI medium (Cat. # B9994; Teknova, Inc., Hollister, Calif.). Plate counts were performed on BHI agar plates (Cat. # B1010; Teknova, Inc., Hollister, Calif.).

Preparation of Whole Cell Lysates by Water Lysis Method 10 ml of BHI was inoculated with *E. coli* and incubated overnight at 37° C. Serial 1:10 dilutions were made in BHI medium to a final concentration of approximately $10^2$ cells/ml, based on an estimated starting concentration of $3 \times 10^9$ cells/ml.

From dilutions at approximately $10^3$ and $10^2$ cells/ml, 100 μl was spread on a BHI agar plate. Plates were incubated at 37° C. for 18 hrs and the number of colonies was counted to determine cfu per each dilution.

From each dilution containing approximately $10^9$ cells/ml to $10^5$ cells/ml, 5 μl of diluted cells was transferred into 95 μl distilled, deionized water plus 5 μl 20 U/μl RNase inhibitor (Cat. # N808-0119, Applied Biosystems, Foster City, Calif.) in 0.5 ml thin-walled PCR tubes. Cells were incubated for 15 min at 75° C. in the GeneAmp PCR System 9700 (PE Applied Biosystems, Foster City, Calif.). The resulting cell sample lysate was chilled on ice and then immediately used in RT-PCR reactions below.

RT-PCR

Real time Reverse Transcription-PCR (RT-PCR) was performed on a Sequence Detection System (SDS) instrument (Applied Biosystems, Foster City, Calif./USA, Model 7900). 20 μl reactions were set up as follows both with and without Reverse Transcriptase (+ or −Rt): 10 μl TaqMan Universal PCR 2× Master Mix (AppliedBiosystems, Foster City, Calif./USA, #4324018), 0.4 μl Rnase Inhibitor (AppliedBiosystems, Foster City, Calif./USA, #N808-0119, 20 U/ul), 0.01 μl MultiScribe Reverse Transcriptase (AppliedBiosystems, Foster City, Calif./USA, #4311235), 0.1 ul 16S-2455F 100 µM primer (Sigma Genosys, Woodlands, Tex./USA, 5' GCT-GATACCGCCCAAGAGTTC: SEQ ID No:6), 0.2 µl 16S-2523R 100 µM primer (Sigma Genosys, Woodlands, Tex./USA, 5' CAGGATGTGATGAGCCGACAT: SEQ ID No:7), 0.05 µl 16S-2479T 100 µM TaqMan TAMRA Probe (AppliedBiosystems, Foster City, Calif./USA, #450025,6 FAM-TCGACGGCGGTGTTTGGCAC: SEQ ID No:8), 7.24 µl Molecular Biology Grade water (Eppendorf AG, Hamburg/Germany #0032006.302) and 2 µl sample lysate. All reactions were run in triplicate Reactions were carried out in a thermal cycler with the following conditions: 50° C. for 10 min, 95° C. for 10 min, followed by 40 cycles of 95° C. for 15 sec+60° C. for 1 min. Real time fluorescence data was collected each cycle. The TaqMan 5'-3' exonuclease assay was run as described previously in Example 7.

The CT values shown in Table 17 follow a pattern that would be predicted for detection of purified target RNA and DNA. There was a dose response or increase in CT as the amount of target RNA or DNA was decreased across the 1:10 dilution series. This result means that as the samples were diluted it took increasingly longer for the reporter fluorescence to reach the threshold determined by the instrument. Thus the direct assay of the lysed $E.\ coli$ bacterial cell samples showed detection of target RNA by RT-PCR in a pattern comparable to detection expected from purified nucleic acid samples.

Lower CT values were observed in the (+) RT data at each lysate concentration compared to the (−) RT data. The lower CT values are an indication of the greater amount of target present in the (+) RT reactions. This correlates well with the fact that there are more copies of 16S rRNA present in the lysates compared to 16S rDNA, and is confirmation that RNA was detected in these reactions. This result indicates RNA targets can be detected directly from the cell lysate without any purification steps in $E.\ coli$.

TABLE 17

*E. coli* Lysate CT Values

| E. coli cfu/test | E. coli 16S (+) RT | E. coli 16S (−) RT |
|---|---|---|
| $3 \times 10^5$ | 16.15 | 20.19 |
| $3 \times 10^4$ | 20.75 | 23.65 |
| $3 \times 10^3$ | 24.82 | 27.86 |
| $3 \times 10^2$ | 27.36 | 30.60 |
| $3 \times 10^1$ | ND | ND |

Example 10

Detection of 16S rRNA Target Directly in Whole Cell Lysates of *Methylomonas* sp. 16A using Real time RT-PCR Strain and Media

*Methylomonas* sp. 16a ATCC PTA-240 was obtained from the American Type Culture Collection (Manassas, Va.). Cells were grown at 30° C. in ammonium liquid "BTZ" growth medium (see tables 18 and 19), with methane as the carbon source *Methylomonas* sp. 16a was grown in a serum stoppered Wheaton bottle (Wheaton Scientific; Wheaton, Ill.) using a gas/liquid ratio of at least 8:1 (i.e., 10 mL of ammonium liquid "BTZ" growth medium in a Wheaton bottle of 80 mL total volume). The standard gas phase for cultivation contained 25% methane in air.

TABLE 18

Solution 1*

| | Molecular Weight | Conc. (mM) | g per L |
|---|---|---|---|
| Nitriloacetic acid | 191.10 | 66.90 | 12.80 |
| $CuCl_2 \times 2H_2O$ | 170.48 | 0.15 | 0.0254 |
| $FeCl_2 \times 4H_2O$ | 198.81 | 1.50 | 0.30 |
| $MnCl_2 \times 4H_2O$ | 197.91 | 0.50 | 0.10 |
| $CoCl_2 \times 6H_2O$ | 237.90 | 1.31 | 0.312 |
| $ZnCl_2$ | 136.29 | 0.73 | 0.10 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.70 | 0.77 | 0.184 |

*Mix the gram amounts designated above in 900 mL of $H_2O$, adjust to pH = 7.0, and add $H_2O$ to a final volume of 1 L. Keep refrigerated.

TABLE 19

Ammonium Liquid Medium (BTZ)**

| | MW | Conc. (mM) | g per L |
|---|---|---|---|
| $NH_4Cl$ | 53.49 | 10 | 0.537 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7.0) | 238.3 | | 50 mL |
| Solution 1 | | | 10 mL |

**Dissolve in 900 mL $H_2O$. Adjust to pH = 7.0, and add $H_2O$ to give a final volume of 1 L.

Preparation of Whole Cell Lysates by Water Lysis Method 10 ml of BTZ medium was inoculated with *Methylomonas* sp. 16A and incubated overnight at 30° C. Serial 1:10 dilutions were made in BTZ medium to a final concentration of approximately $10^5$ cells/ml, based on an estimated starting concentration of $3 \times 10^9$ cells/ml.

From each dilution containing approximately $10^9$ cells/ml to $10^5$ cells/ml, 5 µl of diluted cells was transferred d into 95 µl distilled, deionized water plus 5 µl 20 U/µl RNase inhibitor (Cat. # N808-0119, Applied Biosystems, Foster City, Calif.) in 0.5 ml thin-walled PCR tubes. Cells were incubated for 15 min at 75° C. in the GeneAmp PCR System 9700 (PE Applied Biosystems, Foster City, Calif.). The resulting cell sample lysate was chilled on ice and then immediately used in RT-PCR reactions below.

RT-PCR

Real time Reverse Transcription-PCR (RT-PCR) was performed on a Sequence Detection System (SDS) instrument (Applied Biosystems, Foster City, Calif./USA, Model 7900). 20 µl reactions were set up as follows both with and without Reverse Transcriptase (+ or −RT): 10 µl TaqMan Universal PCR 2× Master Mix (AppliedBiosystems, Foster City, Calif./USA, #4324018), 0.4 µl Rnase Inhibitor (AppliedBiosystems, Foster City, Calif./USA, #N808-0119, 20 U/ul), 0.01 µl MultiScribe Reverse Transcriptase (AppliedBiosystems, Foster City, Calif./USA, #4311235), 0.1 ul 16S-1108F 100 µM primer (Sigma Genosys, Woodlands, Tex./USA, 5' TTGCCAGCGCGTCATG: SEQ ID No:9), 0.2 µl 16S-1169R 100 µM primer (Sigma Genosys, Woodlands, Tex./USA, 5' CCACCTTCCTCCGGTTTATCA: SEQ ID No:10), 0.05 µl 16S-1125T 100 µM TaqMan TAMRA Probe (AppliedBiosystems, Foster City, Calif./USA, #450025,6 FAM-CGGGMCTCTAGGGAGACTGCCG: SEQ ID No:11), 7.24 μl Molecular Biology Grade water (Eppendorf AG, Hamburg/Germany #0032006.302) and 2 μl sample lysate. All reactions were run in triplicate.

Reactions were carried out in a thermal cycler with the following conditions: 50° C. for 10 min, 95° C. for 10 min, followed by 40 cycles of 95° C. for 15 sec+60° C. for 1 min. Real time fluorescence data was collected each cycle. The TaqMan 5'-3' exonuclease assay was run as described previously in Example 7.

The CT values shown in Table 20 follow a pattern that would be predicted for detection of purified target RNA and DNA. There was a dose response or increase in CT as the amount of target RNA or DNA was decreased across the 1:10 dilution series. This result means that as the samples were diluted it took increasingly longer for the reporter fluorescence to reach the threshold determined by the instrument. Thus the direct assay of the lysed *Methylomonas* sp. 16a bacterial cell samples showed detection of target RNA by RT-PCR in a pattern comparable to detection expected from purified nucleic acid samples.

Lower CT values were observed in the (+) RT data at each lysate concentration compared to the (−) RT data. The lower CT values are an indication of the greater amount of target present in the (+) RT reactions due to the generation of cDNA from the RNA template. The lower CTs correlate with the fact that there are more copies of 16S rRNA present in the lysates compared to 16S rDNA, and is confirmation that RNA was being detected in these reactions. This result indicates RNA targets can be detected directly from the cell lysate without any purification steps in another gram-negative bacteria, *Methylomonas* spp. Strain 16a.

TABLE 20

*Methylomonas* Lysates Real Time CT Values

| *Methylomonas* sp. 16a estimated cells/ml | *Methylomonas* sp. 16a 16S (+) RT | *Methylomonas* sp. 16a 16S (−) RT |
|---|---|---|
| $3 \times 10^4$ | 17.20 | 20.01 |
| $3 \times 10^3$ | 20.10 | 23.38 |
| $3 \times 10^2$ | 23.26 | 26.78 |
| $3 \times 10^1$ | 26.58 | 30.33 |

Example 11

Detection of 16S rRNA Target Directly in Whole Cell Lysates of *Listeria innocua* in the Presence of Other Bacteria and Ground Beef using Real Time RT-PCR This example demonstrates the detection of *Listeria innocua* CLIP11262 (ATCC BAA-680) present on the surfaces of materials which simulate contact surfaces encountered in food processing plants, including food microflora and matrix materials.

A 120 grit 316 stainless steel surface was sterilized by wiping with a Hype-Wipe disinfecting towel with bleach (Current Technologies Inc, Crawfords, Ind., Catalog # 9103) followed by a sterile water wash. The surface was marked with two grids, each including eight 1 inch×1 inch squares. (See Table 21 and Table 22 for layout.)

TABLE 21

Food treated surface grid.

| Test Method/Palcam Enrichment | | FSIS/UVM enrichment | |
|---|---|---|---|
| A | C | E | G |
| (−) control = 1f | *L. innocua* = 3f | (−) control = 5f | *L. innocua* = 7f |
| B | D | F | H |
| (−) control = 2f | *L. innocua* = 4f | (−) control = 6f | *L. innocua* = 8f |

TABLE 22

Control surface grid.

| Test Method/Palcam Enrichment | | FSIS/UVM enrichment | |
|---|---|---|---|
| A | C | E | G |
| (−) control = 1 | *L. innocua* = 3 | (−) control = 5 | *L. innocua* = 7 |
| B | D | F | H |
| (−) control = 2 | *L. innocua* = 4 | (−) control = 6 | *L. innocua* = 8 |

A single colony of *Listeria innocua* was inoculated into an 8 ml BHI tube (Becton Dickinson, Franklin Lakes, N.J., Catalog # 220837) and incubated at 37° C. for about 17 hours until stationary phase was reached. The culture was then serially diluted in BHI to give a final concentration of $7.3 \times 10^5$ cells/ml. 50 μl of this diluted suspension were applied to give a final concentration of cells on the surface of $3.65 \times 10^4$ cells in the 1"×1" square. The cell suspension was applied with a pipette and spread gently using a pipette tip over each 1 inch by 1 inch square area of the prepared stainless steel surface grids labeled C, D, G, and H. The surface was allowed to dry overnight (18 hours) at room temperature. The control squares labeled A, B, E and F in each grid had no application of *L. innocua*.

Approximately 10 grams of store bought 10% fat lean ground beef stored at 4° C. was homogenized (Ultra Turrax T-25 Basic homogenizer, IKA-Werke, Wilmington, N.C.) in 90 ml of phosphate buffer (PML Microbiologicals, Wilsonville, Oreg., Catalog # B8098). 100 μl of this homogenate was applied by pipette to each square in Table 21 (the food treated surface). The food homogenate was allowed to dry for 1 hour prior to sample collection. Total plate counts of the food homogenate preparation were measured by serial dilution and plating onto Trypticase Soy Agar (TSA) as described in Example 1. TSA plates were incubated for 48 hours at 37° C. The microbial counts from the ground beef homogenate indicated that microorganisms were present in the ground beef at a level of $1 \times 10^4$ cells/gram. Thus the 100 μl sample applied to each square contained approximately $1 \times 10^2$ microorganisms.

After allowing the food homogenate to dry for 1 hour, samples were collected by surface swabbing using cotton tips affixed to a wood stick, delivered in a pre-sterilized package (Puritan, Guilford, Me., Catalog # REF 25-806 1WC). Swabs were pre-moistened with neutralizing broth (D/E Neutralizing broth). The samples were collected (both food samples and controls) by vigorous swabbing of a 1"×1" section (~5 cm²) of the contaminated surface.

Swabs were analyzed by both the USDA-FSIS reference method and by RT-PCR. For the FSIS method, each swab was added to a tube with 10 ml+/−0.5 ml of UVM broth. The swab was left in the tube (breaking off the end of swab as necessary to replace the cap) and vortexed to mix. The tubes were incubated for 22 h+/−2 h at 30° C.+/−2° C. Following incubation, 100 μl+/−2 μl of UVM culture was removed and added to 10 ml+/−0.5 ml Fraser Broth (FB). The FB was incubated at 37° C.+/−2° C., for 26 h+/−2 h. Following incubation, the FB was examined for darkening, indicating the presence of *Listeria*. All swabs samples collected from *L. innocua* treated grid squares did show darkening, indicated as a "yes" in the FSIS test results in Table 23, and all squares that were not treated with *L. innocua* showed no darkening, a negative result.

TABLE 23

USDA-FSIS results

| Sample | Treatment | Listeria | Incubation Time | USDA-FSIS (+) |
|---|---|---|---|---|
| 5 | No food | No | 48 h in FB | No |
| 6 | No food | No | 48 h in FB | No |
| 7 | No food | Yes | 48 h in FB | Yes |
| 8 | No food | Yes | 48 h in FB | Yes |
| 5F | Food | No | 48 h in FB | No |
| 6F | Food | No | 48 h in FB | No |
| 7F | Food | Yes | 48 h in FB | Yes |
| 8F | Food | Yes | 48 h in FB | Yes |

FB—Fraser Broth

For RT-PCR assay, each swab was added to 10 ml+/−0.5 ml of Palcam Plus broth. The swab was left in the tube (breaking off end of the swab as necessary to replace the cap) and vortexed to mix. The tubes were incubated for 48 hours+/−2 h at 37° C.+/−2° C. The cultures were sampled for testing by RT-PCR at 24 hours and 48 hours by removal of 1 ml aliquots. The aliquots were lysed by heat treatment at 75° C. for 10 min. Lysates were tested using RT-PCR as described in Example 2.

24 and 48 hour RT-PCR results are shown in Tables 24 and 25, respectively. All samples collected from *Listeria* treated squares were positive at both time points in the RT-PCR assay and by the USDA-FSIS reference method (Table 23). All samples collected from squares with no *Listeria* treatment were negative by RT-PCR and the USDA-FSIS method (Table 23). Thus the presence of a food matrix that includes contaminating bacteria did not affect the accuracy of the heat lysis RT-PCR assay.

TABLE 24

24 Hour Real-Time RT-PCR Results
24 hour sampling time point

| Sample Name | Media | Food Treatment | Listeria Treatment | Mean CT n = 3 | Std dev | Mean derivative Peak | Std dev |
|---|---|---|---|---|---|---|---|
| 1 | Palcam Plus | No | No | ND | | 2.88 | 0.56 |
| 2 | Palcam Plus | No | No | ND | | 3.04 | 0.16 |
| 3 | Palcam Plus | No | Yes | 23.58 | 0.73 | 155.86 | 14.81 |
| 4 | Palcam Plus | No | Yes | 23.85 | 2.96 | 136.55 | 38.26 |
| 1F | Palcam Plus | Yes | No | ND | | 3.55 | 0.45 |
| 2F | Palcam Plus | Yes | No | ND | | 2.68 | 0.32 |
| 3F | Palcam Plus | Yes | Yes | 24.42 | 1.67 | 144.49 | 22.68 |
| 4F | Palcam Plus | Yes | Yes | 24.60 | 0.43 | 147.75 | 7.04 |

ND—Not Detectable

TABLE 25

48 Hour Real-Time RT-PCR Results
48 hour sampling time point

| Sample Name | Media | Food Treatment | Listeria Treatment | Mean CT n = 3 | Std dev | Mean derivative Peak | Std dev |
|---|---|---|---|---|---|---|---|
| 1 | Palcam Plus | No | No | ND | | 2.82 | 0.6 |
| 2 | Palcam Plus | No | No | ND | | 3.40 | 0.8 |
| 3 | Palcam Plus | No | Yes | 29.67 | 2.30 | 99.35 | 19.8 |
| 4 | Palcam Plus | No | Yes | 28.24 | 1.63 | 103.15 | 12.8 |
| 1F | Palcam Plus | Yes | No | ND | | 2.39 | 0.9 |
| 2F | Palcam Plus | Yes | No | ND | | 2.71 | 0.3 |
| 3F | Palcam Plus | Yes | Yes | 25.11 | 0.57 | 135.28 | 8.3 |
| 4F | Palcam Plus | Yes | Yes | 25.23 | 0.65 | 133.80 | 9.6 |

ND—Not Detectable

Example 12

Direct Detection of 16S rRNA Targets in Whole Cell Lysates of Bacteria using Only Reverse Transcription The product of an RT reaction is detected without undergoing a PCR step.

Strain and Media

*L. innocua* as described from Example 2 is used for this purpose. Cells are grown at 37° C. in BHI medium (Cat. # B9994; Teknova, Inc., Hollister, Calif.). Plate counts are performed on BHI agar plates (Cat. # B1010; Teknova, Inc., Hollister, Calif.).

Preparation of Whole Cell Lysates by Water Lysis Method 10 ml of BHI ars inoculated with *L. innocua* and incubated overnight at 37° C. Serial 1:10 dilutions are made in BHI medium to a final concentration of approximately $10^2$ cells/ml, based on an estimated starting concentration of $3 \times 10^9$ cells/ml.

From dilutions at approximately $10^9$ and $10^2$ cells/ml, 100 µl is spread on a BHI agar plate. Plates are incubated at 37° C. for 18 hrs and the number of colonies is counted to determine cfu per each dilution.

From each dilution containing approximately $10^9$ cells/ml to $10^5$ cells/ml, 5 µl of diluted cells are transferred into 95 µl distilled, deionized water plus 5 µl 20 U/µl RNase inhibitor (Cat. # N808-0119, Applied Biosystems, Foster City, Calif.) in 0.5 ml thin-walled PCR tubes. Cells are incubated for 15 min at 75° C. in the GeneAmp PCR System 9700 (PE Applied Biosystems, Foster City, Calif.). The resulting cell sample lysate is chilled on ice and then immediately used in reverse transcription reactions below.

RT Reactions

Reverse transcription is performed under the following conditions:

1. The specific primer (1-6 µg) for RT is added to cell lysate (from 5 to 20 µl). The Lis-R primer (SEQ ID NO: 2) is used as a primer for detection of *Listeria innocua* 16S rRNA. The volume is adjusted to 25 µl with RNase and DNase-free water.
2. 14 µl of labeling mixture are added. This mixture contains 8 µl of 5× enzyme buffer, 4 µl DTT (0.1 M), and 2 µl of 20× dye mixture. The dye mixture contains 2 mM of each dATP, dGTP, and dTTP, 1 mM dCTP, and 1 mM of Cy3-dCTP or Cy5-dCTP.
3. The mixture is incubated for 10 min at room temperature for annealing.
4. 1 or 1.4 µl (200-300 units) of reverse transcriptase is added and the reaction is incubated in the appropriate temperature for the enzyme used. For example, for Superscript II enzyme, incubation temperature is 42° C.
5. cDNA purification is carried out with a DNA purification kit. For example, Qiagen PCR kit may be used for this purpose. Alternatively, fluorescent labeled primers are used in the RT reaction, and only unlabeled dCTP is added.

Detection of the cDNA Product

The cDNA RT product labeled with fluorescent dyes is detected in one of several ways. It can be measured with a spectrophotometer. For example, Cy3 label DNA molecules are routinely measured at the wavelength of 550 nm with an extinction coefficient of 150,000 $M^{-1}$, while Cy5 labeled DNA is measured at 650 nm with an extinction coefficient of 250,000 $M^{-1}$. A more sensitive way to directly detect the labeled DNA is to hybridize the products against target DNA sequence molecules that are immobilized in a matrix, such as a nylon membrane or glass slides. The signals after hybridization can then be scanned with a laser scanner with appropriate filtering to detect the specific dye used. This method is well known in the art, especially in DNA microarray technology.

Another sensitive method to detect cDNA is to use primers that are linked to particles with a large number of signal generating molecules. Alternatively, cDNA generated from RT can be amplified by coupling of in vitro transcription rather than PCR. For example, the T7 promoter region can be incorporated into the primer used for the RT reaction. A T7 in vitro transcription kit can then be used to generate a large amount of RNA to increase the detection sensitivity. The T7 in vitro transcriptional kit can be purchased from Ambion (2130 Woodward, Austin, Tex.) or other commercial sources. Through a described method, the cDNA product of the RT reaction with *Listeria innocua* cells is detected.

What is claimed is:

1. A method for the direct detection of a diagnostic target RNA from a bacteria, comprising the steps of:
   a) providing a sample comprising at least a portion of at least one bacterial cell, said portion of said cell comprising a diagnostic target RNA;
   b) contacting the sample with an RT-PCR composition to form an RT-PCR reaction mixture;
   c) thermocycling the RT-PCR reaction mixture, whereby a diagnostic target DNA product is amplified; and
   d) detecting the amplified diagnostic target DNA product of (c), with the proviso that no step includes RNA purification and wherein the sample of (a) does not contain an exogenously added RNase inhibitor.

2. A method for the direct detection of a diagnostic target RNA from a bacteria, comprising the steps of:
   a) providing a sample comprising at least a portion of at least one bacterial cell, said portion of said cell comprising a diagnostic target RNA;
   b) contacting the sample with an RT reaction composition to form an RT reaction mixture under conditions, whereby a diagnostic DNA product is transcribed from the RNA;
   c) detecting the diagnostic target DNA product, with the proviso that no step includes RNA purification and wherein the sample of (a) does not contain an exogenously added RNase inhibitor.

3. A method according to claim 2, further comprising after step (b), the steps of:
   contacting the diagnostic DNA product with a PCR composition to result in a PCR reaction mixture; and
   thermocycling the resultant PCR reaction mixture, whereby the diagnostic target DNA product is amplified.

4. A method according to claim 2, wherein the detecting comprises incorporating or attaching a label to the diagnostic target DNA product.

5. A method according to claim 3, wherein the label is selected from the group consisting of fluorescent moieties, chemiluminescent moieties, particles, enzymes, radioactive tags and light emitting moieties.

6. A method according to any of claims 1, 2 or 3, further comprising contacting the sample with a lysing agent.

7. A method according to claim 6, wherein the lysing agent is selected from the group consisting of a lysis buffer and high temperature.

8. A method according to claim 6, wherein the lysing agent is selected from the group consisting of a chemical, an enzyme and physical shearing.

9. A method according to claim 8, wherein the enzyme is selected from the group consisting of lysozyme, glucolase, zymolose, lyticase and viral endolysins.

10. A method according to claim 9, wherein the viral endolysin is selected from the group consisting of endolysins from bacteriophages or prophages and combinations of these.

11. A method according to claim 9, wherein the viral endolysin is selected from the group consisting of endolysins from *Listeria* bacteriophages A118 and PLY118, endolysins from bacteriophage PM2, endolysins from the *B. subtilis* bacteriophage PBSX, endolysins from *Lactobacillus* prophages Lj928, Lj965 and bacteriophage Phiadh, endolysin (Cpl-1) from the *Streptococcus pneumoniae* bacteriophage Cp-1, the bifunctional peptidoglycan lysin of *Streptococcus agalactiae* bacteriophage B30, two-component cell lysis genes holWMY and lysWMY of the Staphylococcus warneri M phage varphiWMY and combinations of these.

12. A method according to claim 8, wherein the physical shearing is produced by zirconia-silica beads or a French press.

13. A method according to any of claims 1, 2 or 3, wherein the sample is heated to a temperature in the range of about 50° C. to less than or about 100° C.

14. A method according to any of claims 1, 2 or 3, wherein the diagnostic target RNA is selected from the group consisting of mRNAs, rRNAs, tRNAs and small RNA species.

15. A method according to claim 14, wherein the rRNAs are selected from the group consisting of 5S RNA, 16S RNA, and 23S RNA.

16. A method according to any of claims 1, 2 or 3, wherein the at least one bacterial cell is a member of a genus selected from the group consisting of *Listeria, Escherichia, Salmonella, Campylobacter, Clostridium, Helicobacter, Mycobacterium, Staphylococcus, Camplobacter, Enterococcus, Bacillus, Neisseria, Shigella, Streptococcus, Vibrio, Yersinia, Bordetella, Borrelia*, and *Pseudomonas*.

17. A method according to any of claims 1, 2, 3 or 4, wherein the sample is selected from the group consisting of food, meat, flesh products, dairy products, fruit, ground beef and combinations of these.

18. A method according to claims 1, 2, 3, or 4, wherein the sample is selected from the group consisting of samples taken from a food processing context and samples taken from a medical context.

* * * * *